US011241580B2

(12) United States Patent
Esteller et al.

(10) Patent No.: US 11,241,580 B2
(45) Date of Patent: Feb. 8, 2022

(54) ARTIFACT REDUCTION IN A SENSED NEURAL RESPONSE

(71) Applicant: Boston Scientific Neuromodulation Corporation, Valencia, CA (US)

(72) Inventors: Rosana Esteller, Santa Clarita, CA (US); Pranjali Borkar, Atlanta, GA (US); Tianhe Zhang, Studio City, CA (US); Kiran K. Gururaj, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 111 days.

(21) Appl. No.: 16/419,951

(22) Filed: May 22, 2019

(65) Prior Publication Data

US 2019/0366094 A1 Dec. 5, 2019

Related U.S. Application Data

(60) Provisional application No. 62/679,259, filed on Jun. 1, 2018.

(51) Int. Cl.
*A61N 1/36* (2006.01)

(52) U.S. Cl.
CPC ..... *A61N 1/36135* (2013.01); *A61N 1/36014* (2013.01); *A61N 1/36062* (2017.08); *A61N 1/36175* (2013.01)

(58) Field of Classification Search
CPC ............ A61N 1/36135; A61N 1/36062; A61N 1/36014; A61N 1/36175
See application file for complete search history.

(56) References Cited

U.S. PATENT DOCUMENTS 5,184,615 A * 2/1993 Nappholz ............ A61N 1/3622
607/14
5,697,958 A 12/1997 Paul et al.
(Continued)

FOREIGN PATENT DOCUMENTS

WO 2015/077362 A1 5/2015
WO 2017/100866 6/2017
(Continued)

OTHER PUBLICATIONS

Abbas, P.J. et al., "Summary of Results Using the Nucleus CI24M Implant to Record the Electrically Evoked Compound Action Potential," Ear and Hearing: Official Journal of the American Auditory Soc, Lippincott Williams & Wilkins, Wolters Kluwer Health, vol. 20, No. 1, Feb. 1, 1999, pp. 45-59.
(Continued)

*Primary Examiner* — Michael W Kahelin
(74) *Attorney, Agent, or Firm* — Lewis & Reese, PLLC

(57) ABSTRACT

Methods and systems for providing neuromodulation therapy are disclosed. The methods and systems are configured to sense an evoked neural response and use the evoked neural response as feedback for providing neuromodulation therapy. Methods of reducing stimulation artifacts that obscure the sensed evoked neural response are disclosed. The methods of artifact reduction include recording a stimulation artifact in the absence of an evoked neural response, aligning and scaling the stimulation artifact with respect to the obscured signal, and subtracting the aligned and scaled artifact from the obscured signal.

17 Claims, 10 Drawing Sheets

(56) References Cited

U.S. PATENT DOCUMENTS

| | | |
|---|---|---|
| 5,702,429 A | 12/1997 | King |
| 5,902,236 A | 5/1999 | Iversen |
| 5,902,249 A | 5/1999 | Lyster |
| 5,913,882 A | 6/1999 | King |
| 6,181,969 B1 | 1/2001 | Gord et al. |
| 6,516,227 B1 | 2/2003 | Meadows et al. |
| 7,024,247 B2 | 4/2006 | Gliner et al. |
| 7,424,322 B2 | 9/2008 | Lombardi et al. |
| 7,450,992 B1 | 11/2008 | Cameron |
| 8,255,057 B2 | 8/2012 | Fang et al. |
| 8,335,664 B2* | 12/2012 | Eberle .............. G01N 33/4836 702/190 |
| 8,352,030 B2* | 1/2013 | Denison .............. G01D 5/24 607/17 |
| 8,606,362 B2 | 12/2013 | He et al. |
| 8,620,436 B2 | 12/2013 | Parramon et al. |
| 8,768,453 B2 | 7/2014 | Parramon et al. |
| 9,044,155 B2 | 6/2015 | Strahl |
| 9,061,140 B2 | 6/2015 | Shi et al. |
| 9,119,964 B2 | 9/2015 | Marnfeldt |
| 9,155,892 B2 | 10/2015 | Parker et al. |
| 9,248,274 B2 | 2/2016 | Troosters et al. |
| 9,248,279 B2 | 2/2016 | Chen et al. |
| 9,265,431 B2 | 2/2016 | Hincapie Ordonez et al. |
| 9,302,112 B2 | 4/2016 | Bornzin et al. |
| 9,381,356 B2 | 7/2016 | Parker et al. |
| 9,386,934 B2 | 7/2016 | Parker et al. |
| 9,403,013 B2 | 8/2016 | Walker et al. |
| 9,409,020 B2 | 8/2016 | Parker |
| 9,526,897 B2 | 12/2016 | Chen et al. |
| 9,533,148 B2 | 1/2017 | Carcieri et al. |
| 9,731,116 B2 | 8/2017 | Chen |
| 9,872,990 B2 | 1/2018 | Parker et al. |
| 9,974,455 B2 | 5/2018 | Parker et al. |
| 10,076,667 B2 | 9/2018 | Kaula et al. |
| 2002/0156513 A1 | 10/2002 | Borkan |
| 2005/0246004 A1 | 11/2005 | Cameron et al. |
| 2008/0146894 A1 | 6/2008 | Bulkes et al. |
| 2012/0092031 A1 | 4/2012 | Shi et al. |
| 2012/0095519 A1 | 4/2012 | Parramon et al. |
| 2012/0095529 A1 | 4/2012 | Parramon et al. |
| 2013/0289665 A1 | 10/2013 | Marnfeldt et al. |
| 2014/0194772 A1 | 7/2014 | Single et al. |
| 2014/0236042 A1 | 8/2014 | Parker et al. |
| 2014/0296737 A1 | 10/2014 | Parker et al. |
| 2015/0018699 A1 | 1/2015 | Zeng et al. |
| 2015/0119751 A1 | 4/2015 | Stanslaski et al. |
| 2015/0157861 A1 | 6/2015 | Aghassian et al. |
| 2015/0282725 A1 | 10/2015 | Single et al. |
| 2015/0313487 A1* | 11/2015 | Single .............. A61B 5/686 600/554 |
| 2015/0360038 A1 | 12/2015 | Zottola et al. |
| 2016/0166164 A1 | 6/2016 | Obradovic et al. |
| 2016/0287126 A1 | 10/2016 | Parker et al. |
| 2016/0287182 A1* | 10/2016 | Single .............. A61N 1/36139 |
| 2017/0049345 A1 | 2/2017 | Single et al. |
| 2017/0071490 A1* | 3/2017 | Parker .............. A61N 1/36125 |
| 2017/0135624 A1 | 5/2017 | Parker et al. |
| 2017/0216587 A1 | 8/2017 | Parker et al. |
| 2017/0273594 A1* | 9/2017 | Liu .............. A61B 5/4238 |
| 2017/0296823 A1* | 10/2017 | Hershey .............. A61N 1/36128 |
| 2017/0361101 A1 | 12/2017 | Single et al. |
| 2018/0071520 A1 | 3/2018 | Weerakoon et al. |
| 2018/0071527 A1 | 3/2018 | Feldman et al. |
| 2018/0110987 A1 | 4/2018 | Parker et al. |
| 2018/0117335 A1 | 5/2018 | Parker et al. |
| 2018/0132747 A1 | 5/2018 | Parker et al. |
| 2018/0132760 A1 | 5/2018 | Parker et al. |
| 2018/0133459 A1 | 5/2018 | Parker et al. |
| 2018/0140831 A1 | 5/2018 | Feldman et al. |
| 2018/0228391 A1 | 8/2018 | Parker et al. |
| 2018/0228547 A1 | 8/2018 | Parker et al. |
| 2018/0256052 A1 | 9/2018 | Parker et al. |
| 2019/0099602 A1 | 4/2019 | Esteller et al. |

FOREIGN PATENT DOCUMENTS

| | | |
|---|---|---|
| WO | 2017/173493 | 10/2017 |
| WO | 2017/210352 A1 | 12/2017 |
| WO | 2017/219096 | 12/2017 |

OTHER PUBLICATIONS

Nguyen, T.A.K., et al., "Finding Physiological Responses in Vestibular Evoked Potentials," Engineering in Medicine and Biology Society, EMBC, 2011 Annual International Conference of the IEEE, IEEE, Aug. 30, 2011, pp. 2258-2261.

Woo, J., et al., "Improved Noise Reduction in Single Fiber Auditory Neural Responses using Template Subtraction," Journal of Neuroscience Methods, Elsevier Science Publisher B V., vol. 155, No. 2, Sep. 15, 2006, pp. 319-327.

International Search Report and Written Opinion regarding corresponding PCT Application No. PCT/US2019/033603, dated Aug. 16, 2019.

U.S. Appl. No. 62/614,736, filed Jan. 8, 2018, Esteller.
U.S. Appl. No. 62/641,748, filed Mar. 12, 2018, Zhu et al.
U.S. Appl. No. 62/648,231, filed Mar. 26, 2018, Esteller et al.
U.S. Appl. No. 62/650,844, filed Mar. 30, 2018, Marnfeldt et al.
U.S. Appl. No. 62/679,259, filed Jun. 1, 2018, Esteller et al.
U.S. Appl. No. 62/768,617, filed Nov. 16, 2018, Esteller et al.
U.S. Appl. No. 62/825,982, filed Mar. 29, 2019, Wagenbach et al.
U.S. Appl. No. 16/210,794, filed Dec. 5, 2018, Brill et al.

Akhoun, Idrick, et al., "Electrically Evoked Compound Action Potential Artifact Rejection by Independent Component Analysis: Technique Validation," Hear. Res. 302 : 60-73, (2013).

ARM Cortex M0+, manufactured by ARM, retrieved on Jun. 13, 2018, 6 pages, retrieved from <http://developer.arm.com/products/processors/cortex-m/cortex-m0-plus>.

Part No. MSP430, manufactured by Texas Instruments, retrieved on Jun. 13, 2018, 2 pages, retrieved from <http://www.ti.com/microcontrollers/msp430-ultra-low-power-mcus/overview.html?DCMP=MCU other&%25252520HQS=msp430>.

"Precision Spectra™ System Programming Manual," Boston Scientific Corp., 90834018-18 Rev A, 2016, 64 pages.

H. Mino & J. Rubenstein, "Effects of Neural Refractoriness on Spatio-Temporal Variability in Spike Initiations with Eletrical Stimulation," IEEE Trans. on Neural Sys. & Rehabilitation Eng., vol. 14, No. 3, pp. 273-280 (2006).

M. Moffit et al., A Novel 3-Dimensional Algorithm for Model-Based Programming in Spinal Cord Stimuation (SCS): Illumina-3D™, presentation (2013).

M. Hughes, "Fundamentals of Clinical ECAP Measures in Cochlear Implants: Part 1: Use of the ECAP in Speech Processor Programming (2nd Ed.)," Audiology Online (Nov. 8, 2010) (http://www.audiologyonline.com/articles/fundamentalsclinicalecapmeasuresin846).

I. Akhoun et al., "Electrically evoked compound action potential artifact rejection by independent component analysis: Technique validation," Hearing Research 302, pp. 60-73 (2013).

J. Rubinstein et al., "Pseudospontaneous activity: stochastic independence of auditory nerve fibers with electrical stimulation," Hear Res., 127(1-2), pp. 108-118 (1999) (abstract only).

J. Paz, "Physiological Midline Mapping Based on Spinal Cord Stimulation (SCS) Response Using the 32-Contact Paddle Lead," 19th NANS Annual Meeting (Dec. 13-15, 2015).

E.L. Air et al., "Electrophysiologic Monitoring for Placement of Laminectomy Leads for Spinal Cord Stimulation Under General Anesthesia," Neuromodulation: Technology at the Neural Interface, vol. 15(6), pp. 573-580 (2012).

J.L. Shils et al., "Intraoperative Neurophysiologic Methods for Spinal Cord Stimulator Placement Under General Anesthesia," Neuromodulation: Technology at the Neural Interface, vol. 15(6), pp. 560-572 (2012).

A. Taghva et al., "Intraoperative Electromyography as an Adjunct to Sacral Neuromodulation for Chronic Pelvic Pain," Neuromodula-

(56) References Cited

OTHER PUBLICATIONS tion: Technology at the Neural Interface, vol. 18(1), pp. 62-66 (2015).

* cited by examiner

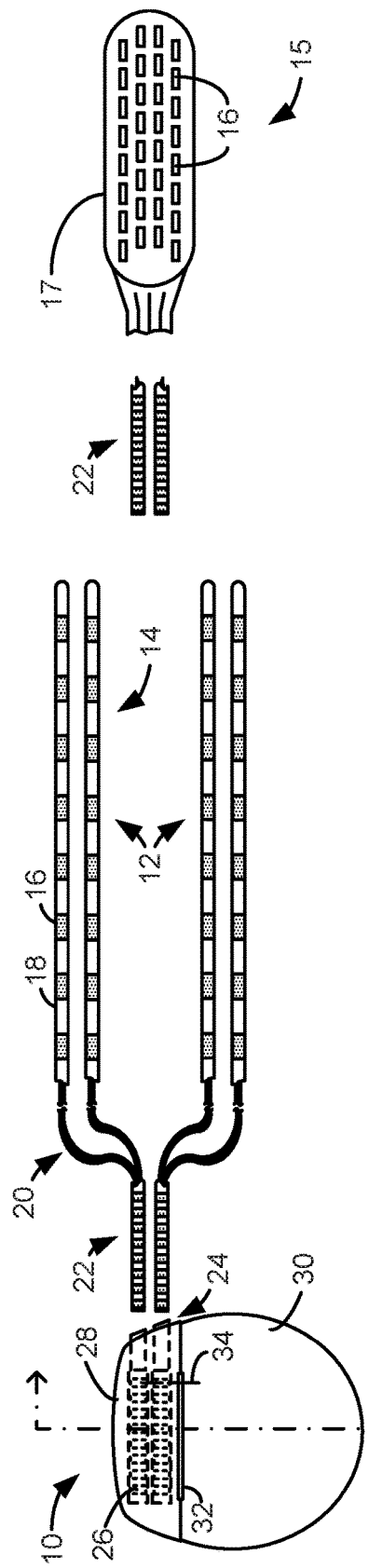
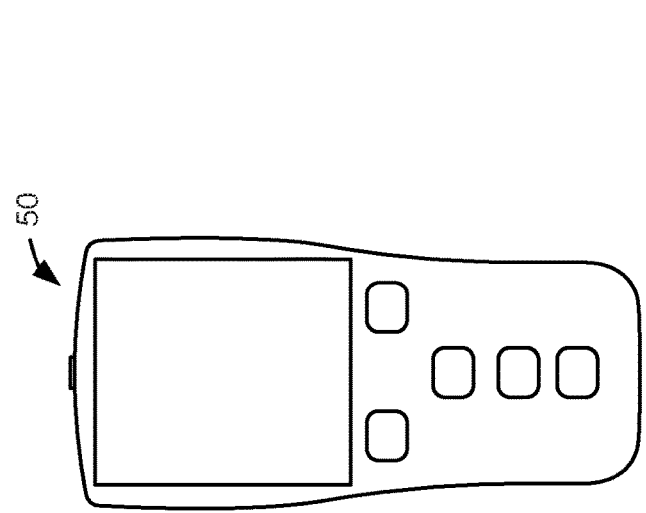
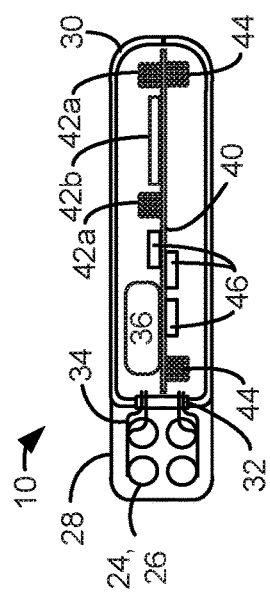
Figure 1A (prior art)
Figure 1B (prior art)
Figure 2 (prior art)

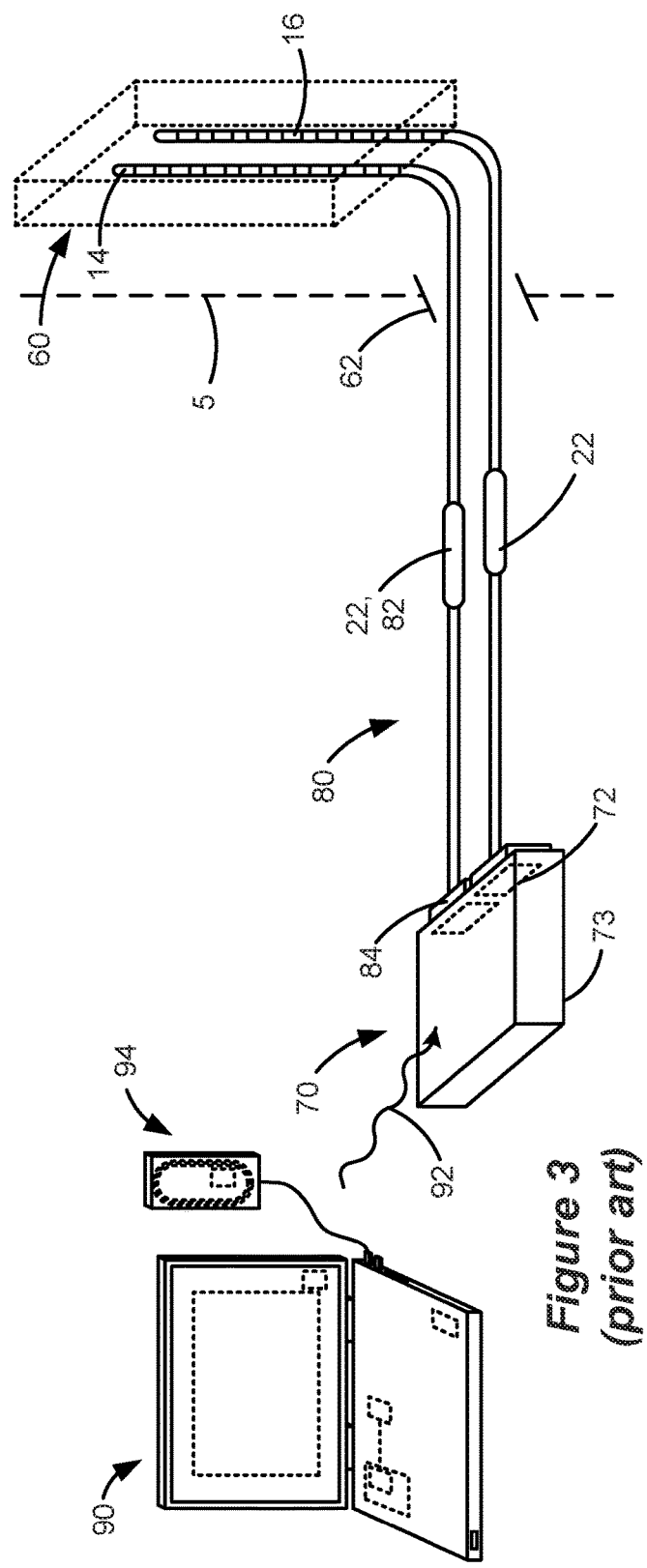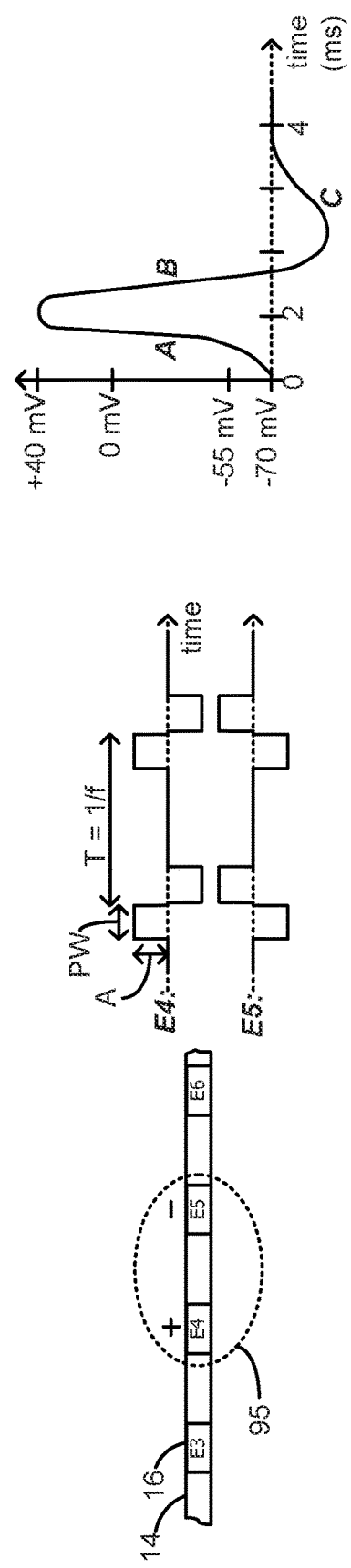

ARTIFACT REDUCTION IN A SENSED NEURAL RESPONSE

CROSS REFERENCE TO RELATED APPLICATIONS

This application is a non-provisional application of U.S. Provisional Patent Application Ser. No. 62/679,259, filed Jun. 1, 2018, which is incorporated herein by reference, and to which priority is hereby claimed.

FIELD OF THE INVENTION

The present invention relates generally to medical device systems, and more particularly to pulse generator systems operable to measure spinal cord potentials (SCPs).

INTRODUCTION

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and Deep Brain Stimulators (DBS) to treat motor and other neurological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any Implantable Medical Device (IPG) or in any IPG system, such as in a Deep Brain Stimulation (DBS) system as disclosed in U.S. Pat. No. 9,119,964.

An SCS system typically includes an Implantable Pulse Generator (IPG) 10 shown in plan and cross-sectional views in FIGS. 1A and 1B. The IPG 10 includes a biocompatible device case 30 is configured for implantation in a patient's tissue that holds the circuitry and battery 36 (FIG. 1B) necessary for the IPG to function. The IPG 10 is coupled to electrodes 16 via one or more electrode leads 14 that form an electrode array 12. The electrodes 16 are configured to contact a patient's tissue and are carried on a flexible body 18, which also houses the individual lead wires 20 coupled to each electrode 16. The lead wires 20 are also coupled to proximal contacts 22, which can be inserted into lead connectors 24 fixed in a header 28 on the IPG 10, which header can comprise an epoxy for example. Once inserted, the proximal contacts 22 connect to header contacts 26 in the lead connectors 24, which are in turn coupled by electrode feedthrough pins 34 through an electrode feedthrough 32 to circuitry within the case 30 (connection not shown).

In the illustrated IPG 10, there are thirty-two lead electrodes (E1-E32) split between four leads 14 (referred to as percutaneous leads), with the header 28 containing a 2×2 array of lead connectors 24 to receive the leads' proximal ends. However, the number of leads and electrodes in an IPG is application specific and therefore can vary. In a SCS application, the electrode leads 14 are typically implanted proximate to the dura in a patient's spinal cord, and when a four-lead IPG 10 is used, these leads can be split with two on each of the right and left sides. The proximal contacts 22 are tunneled through the patient's tissue to a distant location such as the buttocks where the IPG case 30 is implanted, at which point they are coupled to the lead connectors 24. As also shown in FIG. 1A, one or more flat paddle leads 15 can also be used with IPG 10, and in the example shown thirty-two electrodes 16 are positioned on one of the generally flat surfaces of the head 17 of the paddle lead, which surface would face the dura when implanted. In other IPG examples designed for implantation directly at a site requiring stimulation, the IPG can be lead-less, having electrodes 16 instead carried by the case of the IPG for contacting the patient's tissue.

As shown in the cross section of FIG. 1B, the IPG 10 includes a printed circuit board (PCB) 40. Electrically coupled to the PCB 40 are the battery 36, which in this example is rechargeable; other circuitry 46 coupled to top and/or bottom surfaces of the PCB 40, including a microcontroller or other control circuitry necessary for IPG operation; a telemetry antenna—42a and/or 42b—for wirelessly communicating data with an external controller 50 (FIG. 2); a charging coil 44 for wirelessly receiving a magnetic charging field from an external charger (not shown) for recharging the battery 36; and the electrode feedthrough pins 34 (connection to circuitry not shown). If battery 36 is permanent and not rechargeable, charging coil 44 would be unnecessary.

The IPG 10 also includes one or more antennas 42a and 42b for transcutaneously communicating with external programming devices, such as a patient external controller 50 (FIG. 2), or a clinician programmer 90 (FIG. 3). Antennas 42a and 42b are different in shape and in the electromagnetic fields they employ. Telemetry antenna 42a comprises a coil, which can bi-directionally communicate with an external device via a magnetic induction communication link. Telemetry antenna 42b comprises a short-range Radio-Frequency (RF) antenna that operates in accordance with a short-range RF communication standard, such as Bluetooth, BLE, NFC, Zigbee, WiFi (802.11x), and the Medical Implant Communication Service (MICS) or the Medical Device Radiocommunications Service (MDRS).

Implantation of IPG 10 in a patient is normally a multi-step process, as explained with reference to FIG. 3. A first step involves implantation of the distal ends of the lead(s) 14 or 15 with the electrodes 16 into the spinal column 60 of the patient through a temporary incision 62 in the patient's tissue 5. (Only two leads 14 with sixteen total electrodes 16 are shown in FIG. 3 for simplicity). The proximal ends of the leads 14 or 15 including the proximal contacts 22 extend externally from the incision 62 (i.e., outside the patient), and are ultimately connected to an External Trial Stimulator (ETS) 70. The ETS 70 is used during a trial stimulation phase to provide stimulation to the patient, which may last for two or so weeks for example. To facilitate the connection between the leads 14 or 15 and the ETS 70, ETS extender cables 80 may be used that include receptacles 82 (similar to the lead connectors 24 in the IPG 10) for receiving the proximal contacts 22 of leads 14 or 15, and connectors 84 for meeting with ports 72 on the ETS 70, thus allowing the ETS 70 to communicate with each electrode 16 individually. Once connected to the leads 14 or 15, the ETS 70 can then be affixed to the patient in a convenient fashion for the duration of the trial stimulation phase, such as by placing the ETS 70 into a belt worn by the patient (not shown). ETS 70 includes a housing 73 for its control circuitry, antenna, etc., which housing 73 is not configured for implantation in a patient's tissue.

The ETS 70 essentially mimics operation of the IPG 10 to provide stimulation to the implanted electrodes 16, and thus includes contains a battery within its housing along with stimulation and communication circuitry similar to that provided in the IPG 10. Thus, the ETS 70 allows the effectiveness of stimulation therapy to be verified for the patient, such as whether therapy has alleviated the patient's symptoms (e.g., pain). Trial stimulation using the ETS 70 further allows for the determination of particular stimulation program(s) that seems promising for the patient to use once the IPG 10 is later implanted into the patient. A stimulation program may include stimulation parameters that specify for example: which of the electrodes 16 are to be active and used to issue stimulation pulses; the polarity of those active electrodes (whether they are to act as anodes or cathodes); the current or voltage amplitude (A) of the stimulation pulses; the pulse width (PW) of the stimulation pulses; the frequency (f) of the stimulation pulses; the duty cycle (DC) of the stimulation pulses (i.e., the percentage of time that the pulses are asserted relative to the period of the pulses) the shape of the stimulation waveform (e.g., one or more square pulses, one or more ramped pulses, one or more sinusoidal pulses, or even non-pulse-based waveforms, etc.); and other parameters related to issuing a burst of pulses, such as the number of pulses; etc.

The stimulation program executed by the ETS 70 can be provided or adjusted via a wired or wireless link 92 (wireless shown) from a clinician programmer 90. As shown, the clinician programmer 90 comprises a computer-type device, and may communicate wirelessly with the ETS 70 via link 92, which link may comprise magnetic inductive or short-range RF telemetry schemes as already described. Should the clinician programmer 90 lack a communication antenna, a communication head or wand 94 may be wired to the computer which has a communication antenna. Thus, the ETS 70 and the clinician's programmer 90 and/or its communication head 94 may include antennas compliant with the telemetry scheme chosen. Clinician programmer 90 may be as described in U.S. Patent Application Publication 2015/0360038. External controller 50 (FIG. 2) may also communicate with the ETS 70 to allow the patient means for providing or adjusting the ETS 70's stimulation program.

At the end of the trial stimulation phase, a decision is made whether to abandon stimulation therapy, or whether to provide the patient with a permanent IPG 10 such as that shown in FIGS. 1A and 1B. Should it be determined that stimulation therapy is not working for the patient, the leads 14 or 15 can be explanted from the patient's spinal column 60 and incision 62 closed in a further surgical procedure.

By contrast, if stimulation therapy is effective, IPG 10 can be permanently implanted in the patient as discussed above. ("Permanent" in this context generally refers to the useful life of the IPG 10, which may be from a few years to a few decades, at which time the IPG 10 would need to be explanted and a new IPG 10 implanted). Thus, the IPG 10 would be implanted in the correct location (e.g., the buttocks) and connected to the leads 14 or 15, and then temporary incision 62 can be closed and the ETS 70 dispensed with. The result is fully-implanted stimulation therapy solution. If a particular stimulation program(s) had been determined during the trial stimulation phase, it/they can then be programmed into the IPG 10, and thereafter modified wirelessly, using either the external programmer 50 or the clinician programmer 90.

SUMMARY

Embodiments of the disclosure provide a neuromodulation system comprising: a first device comprising a non-transitory computer readable medium configured to cause a microprocessor to: cause one or more electrodes useable for stimulation to issue one or more stimulation waveforms to a patient's neural elements, receive a first signal from a first channel comprising one or more electrodes useable for sensing, the first signal comprising a stimulation artifact overlapping an evoked neural response signal, receive a second signal from a second channel comprising one or more electrodes useable for sensing, the second signal comprising a stimulation artifact not overlapping an evoked neural response signal, and based on the first and second signals, determine a reduced-artifact evoked neural response signal comprising a stimulation artifact less than the stimulation artifact of the first signal.

According to some embodiments, the first channel and the second channel are different. According to some embodiments, the one or more electrodes usable for sensing of the first channel are closer to the one or more electrodes usable for stimulating than are the one or more electrodes usable for sensing of the second channel. According to some embodiments, the first channel and the second channel are the same. According to some embodiments, issuing one or more stimulation waveforms comprises: issuing a first stimulation waveform having sufficient stimulation intensity to evoke a detectable neural response, thereby producing the first signal, and issuing a second stimulation waveform having a stimulation intensity that is insufficient to evoke a detectable neural response, thereby producing the second signal. According to some embodiments, determining a reduced-artifact evoked neural response signal comprises: aligning and scaling the stimulation artifact of the second signal with respect to the stimulation artifact of the first signal, and subtracting the aligned and scaled stimulation artifact of the second signal from the stimulation artifact of the first signal. According to some embodiments, aligning the stimulation artifact of the second signal with respect to the stimulation artifact of the first signal comprises cross-correlation. According to some embodiments, the non-transitory computer readable medium is further configured to cause the microprocessor to determine a beginning and an end of the stimulation artifact using inverse stimulation polarity. According to some embodiments, the first device is an implantable pulse generator (IPG) or an external trial stimulator (ETS). According to some embodiments, the first device is an external device. According to some embodiments, the neuromodulation system further comprises an IPG or an ETS. According to some embodiments, the non-transitory computer readable medium is further configured to cause the microprocessor to determine one or more parameters of the reduced-artifact evoked neural response signal. According to some embodiments, the non-transitory computer readable medium is further configured to cause the microprocessor to alter the one or more stimulation waveforms based on the one or more features determined from the reduced-artifact evoked neural response signal.

Embodiments of the disclosure provide a method of measuring an evoked neural response, the method comprising: causing one or more electrodes useable for stimulation to issue one or more stimulation waveforms to a patient's neural elements, receiving a first signal from a first channel comprising one or more electrodes useable for sensing, the first signal comprising a stimulation artifact overlapping an evoked neural response signal, receiving a second signal from a second channel comprising one or more electrodes useable for sensing, the second signal comprising a stimulation artifact not overlapping an evoked neural response signal, and based on the first and second signals, determining a reduced-artifact evoked neural response signal comprising a stimulation artifact less than the stimulation artifact of the first signal.

According to some embodiments, the first channel and the second channel are different. According to some embodiments, the one or more electrodes usable for sensing of the first channel are closer to the one or more electrodes usable for stimulating than are the one or more electrodes usable for sensing of the second channel. According to some embodiments, the first channel and the second channel are the same. According to some embodiments, issuing one or more stimulation waveforms comprises: issuing a first stimulation waveform having sufficient stimulation intensity to evoke a detectable neural response, thereby producing the first signal, and issuing a second stimulation waveform having a stimulation intensity that is insufficient to evoke a detectable neural response, thereby producing the second signal. According to some embodiments, determining a reduced-artifact evoked neural response signal comprises: aligning and scaling the stimulation artifact of the second signal with respect to the stimulation artifact of the first signal, and subtracting the aligned and scaled stimulation artifact of the second signal from the stimulation artifact of the first signal. According to some embodiments, aligning the stimulation artifact of the second signal with respect to the stimulation artifact of the first signal comprises cross-correlation. According to some embodiments, the method further comprises determining a beginning and an end of the stimulation artifact using inverse stimulation polarity. According to some embodiments, the method further comprises determining one or more parameters of the reduced-artifact evoked neural response signal. According to some embodiments, the method further comprises altering the one or more stimulation waveforms based on the one or more features determined from the reduced-artifact evoked neural response signal.

Embodiments of the disclosure provide a non-transitory computer readable medium configured to cause a microprocessor to: cause one or more electrodes useable for stimulation to issue one or more stimulation waveforms to a patient's neural elements, receive a first signal from a first channel comprising one or more electrodes useable for sensing, the first signal comprising a stimulation artifact overlapping an evoked neural response signal, receive a second signal from a second channel comprising one or more electrodes useable for sensing, the second signal comprising a stimulation artifact not overlapping an evoked neural response signal, and based on the first and second signals, determine a reduced-artifact evoked neural response signal comprising a stimulation artifact less than the stimulation artifact of the first signal.

According to some embodiments, the first channel and the second channel are different. According to some embodiments, the one or more electrodes usable for sensing of the first channel are closer to the one or more electrodes usable for stimulating than are the one or more electrodes usable for sensing of the second channel. According to some embodiments, the first channel and the second channel are the same. According to some embodiments, issuing one or more stimulation waveforms comprises: issuing a first stimulation waveform having sufficient stimulation intensity to evoke a detectable neural response, thereby producing the first signal, and issuing a second stimulation waveform having a stimulation intensity that is insufficient to evoke a detectable neural response, thereby producing the second signal. According to some embodiments, determining a reduced-artifact evoked neural response signal comprises: aligning and scaling the stimulation artifact of the second signal with respect to the stimulation artifact of the first signal, and subtracting the aligned and scaled stimulation artifact of the second signal from the stimulation artifact of the first signal. According to some embodiments, aligning the stimulation artifact of the second signal with respect to the stimulation artifact of the first signal comprises cross-correlation. According to some embodiments, the non-transitory computer readable medium is further configured to cause the microprocessor to determine a beginning and an end of the stimulation artifact using inverse stimulation polarity. According to some embodiments, the non-transitory computer readable medium is further configured to cause the microprocessor to determine one or more parameters of the reduced-artifact evoked neural response signal. According to some embodiments, the non-transitory computer readable medium is further configured to cause the microprocessor to alter the one or more stimulation waveforms based on the one or more features determined from the reduced-artifact evoked neural response signal.

BRIEF DESCRIPTION OF THE DRAWINGS

FIGS. 1A and 1B respectively show an Implantable Pulse Generator (IPG) in plan and cross-sectional views, in accordance with the prior art.

FIG. 2 shows a hand-held external controller for communicating with an IPG, in accordance with the prior art.

FIG. 3 shows a clinician programming system for communicating with an IPG or an External Trial Stimulator (ETS), in accordance with the prior art.

FIGS. 5A and 5B show a stimulation program.

FIG. 6 shows a graph of an action potential of a neuron.

DESCRIPTION

Figure 4A:
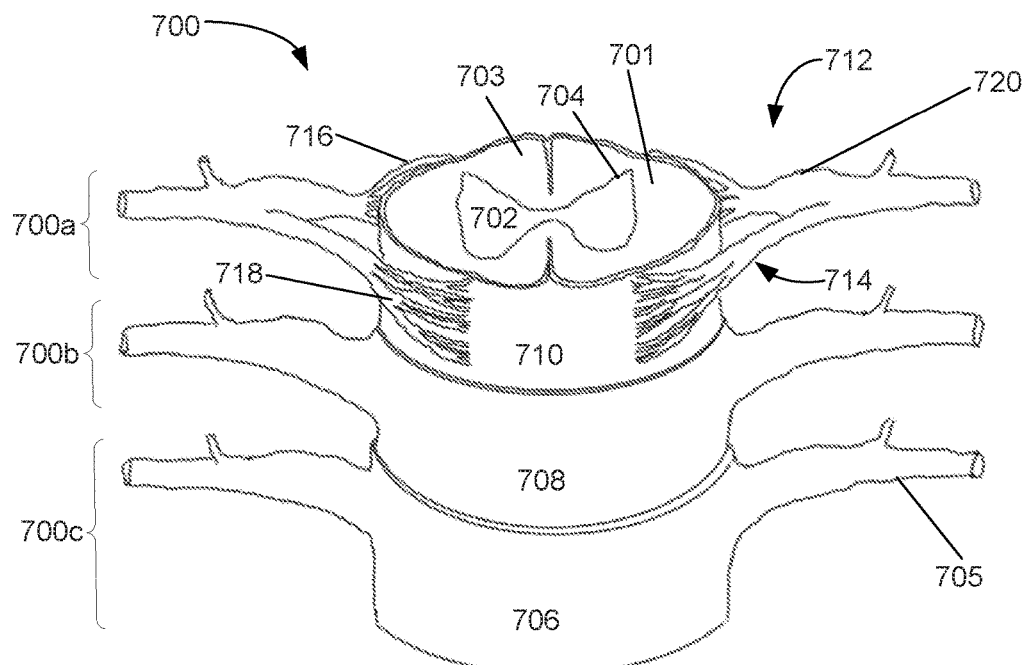
FIGS. 4A and 4B show aspects of the spinal cord and related neural anatomy
Figure 4B:
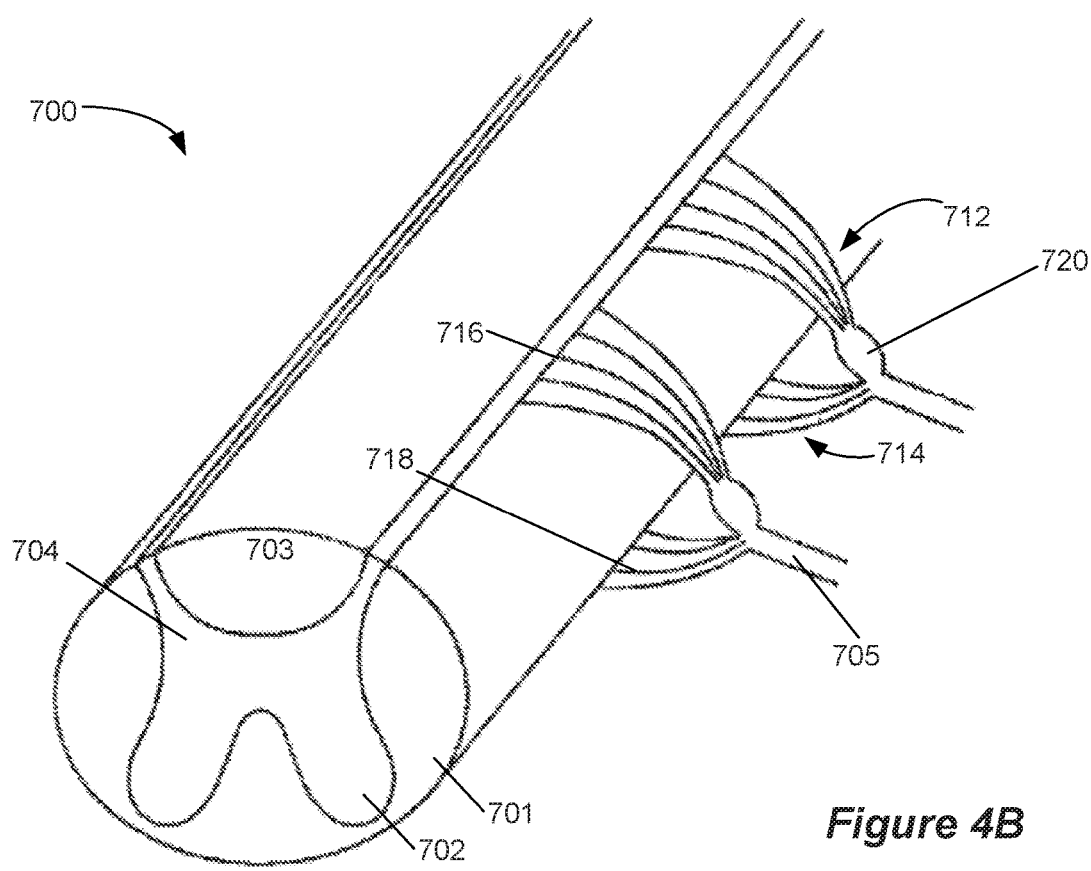

Various embodiments described herein involve neural stimulation. Examples include spinal cord modulation, i.e., spinal cord stimulation (SCS) as well as stimulation and sensing of related neural anatomy. Additional embodiments may include deep brain stimulation (DBS), peripheral nerve stimulation (PNS), and the like. Focusing on SCS, a brief description of the anatomy and physiology of the spinal cord is provided herein to assist the reader. FIGS. 4A and 4B illustrate, by way of example, a portion of a spinal cord 700 including white matter 701 and gray matter 702 of the spinal cord. A typical transverse section of the spinal cord includes a central "butterfly" shaped central area of gray matter 702 substantially surrounded by an ellipse-shaped outer area of white matter 701. The white matter of the dorsal column (DC) 703 includes mostly large myelinated axons that form afferent fibers that run in an axial direction. The dorsal portions of the "butterfly" shaped central area of gray matter are referred to as dorsal horns (DH) 704. In contrast to the DC fibers that run in an axial direction, DH fibers can be oriented in many directions, including laterally with respect to the longitudinal axis of the spinal cord. The gray matter 702 includes cell bodies, synapse, dendrites, and axon terminals.

Referring to FIG. 4A, the spinal cord is enclosed within three layers of tissue, collectively called the meninges. The outer layer of the meninges, called the dura mater 706, is shown in spinal cord segment 700c. The dura mater has been removed in spinal cord segment 700b to reveal the middle meninges, called the arachnoid 708. The innermost meninges, the pia mater 710, is shown in spinal cord segment 700a.

Examples of spinal nerves 705 are also illustrated. Upon removal of the meningeal layers, it is seen that each spinal nerve 705 splits into a dorsal root (DR) 712 and a ventral root 714, each of which comprise subdivisions referred to as rootlets. In FIG. 4A, the dorsal rootlets are labeled 716 and the ventral rootlets are labeled 718. The dorsal root also includes a structure called the dorsal root ganglion (DRG) 720, which comprises cell bodies of the afferent neurons. The dorsal root 712 contains afferent neurons, meaning that they carry sensory signals into the spinal cord, and the ventral root 714 functions as an efferent motor root. The dorsal and ventral roots join to form mixed spinal nerves 705.

While the full mechanisms of pain relief using SCS is not completely understood, it is believed that the perception of pain signals is inhibited via the gate control theory of pain, which suggests that enhanced activity of innocuous touch or pressure afferents via electrical stimulation creates interneuronal activity within the DH 704 of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been targeted for stimulation at an amplitude that provides pain relief.

An example of stimulation pulses as prescribed by an example stimulation program and as executable by the IPG or ETS 70 is illustrated in FIGS. 5A and 5B. As shown in FIG. 5A, electrode E4 is selected as the anode and electrode E5 is selected as the cathode. FIG. 5B illustrates the waveforms of the stimulation pulses delivered by E4 and E5. In the example shown, each stimulation pulse is biphasic, meaning it comprises a first pulse phase followed essentially immediately thereafter by an opposite polarity pulse phase. The pulse width (PW) could comprise the duration of either of the pulse phases individually as shown, or could comprise the entire duration of the biphasic pulse including both pulse phases. The frequency (f) and amplitude (A) of the pulses is also shown. Although not shown, monophasic pulses— having only a first pulse phase but not followed by an active-charge recovery second pulse phase—can also be used. The pulses as shown comprise pulses of constant current, and notice that the amplitude of the current at any point in time is equal but opposite such that current injected into the patient's tissue by one electrode (e.g., E4) is removed from the tissue by the other electrode (E5). Notice also that the area of the first and second pulses phases are equal, ensuring active charge recovery of the same amount of charge during each pulse phase. Although not shown, more than two electrodes can be active at any given time. For example, electrode E4 could comprise an anode providing a +10 mA current pulse amplitude, while electrodes E3 and E5 could both comprise cathodes with −7 mA and −3 mA current pulse amplitudes respectively. Biphasic pulses are particularly beneficial when pulses are issued at higher frequencies, although they may be used at lower frequencies as well.

When a neural fiber is recruited by electrical stimulation, it will issue an action potential—that is, the neural fiber will "fire." An action potential for a typical neural fiber is shown in FIG. 6. Should electrical recruitment from electrical stimulation cause the neural fiber's resting state (e.g., −70 mV as measured from inside the cell) to exceed a threshold (e.g., −55 mV), the neural fiber will depolarize ("A"), repolarize ("B"), and hyperpolarize ("C") before coming to rest again. If electrical stimulation continues, the neural fiber will fire again at some later time, though the neural fiber cannot fire again until after the membrane potential returns to the resting state after the hyperpolarization event. Note that the action potential does not change in magnitude for a given neural fiber. Instead, changing the strength of stimulation may affect the frequency at which action potentials are issued, and may also affect what types of neural fibers are recruited. Each neural fiber is unique in its shape and size, and thus can fire at its own inherent maximum frequency.

Activation of large sensory DC nerve fibers in conventional SCS creates action potentials (i.e., nerve impulses) that propagate orthordromically (toward the brain) and antidromically (away from the brain) from the point of stimulation. The antidromic propagation of action potentials to fiber collaterals and terminals ending in the DH evokes pain control mechanisms within the DH, as described above. The orthodromic propagation of action potentials is responsible for the paresthesia sensation that often accompanies conventional SCS therapy.

The orthodromic and/or antidromic propagation of action potentials can be sensed at electrodes of the lead 14. Consider FIG. 7A, in which electrodes E3, E4 and E5 on lead 14 are used to produce pulses in a bipolar mode of stimulation, with E3 and E5 comprising an anode (+; or source of current) and E4 a cathode (−; or sink of current). Such stimulation produces an electromagnetic (EM) field in a volume 95 of the patient's tissue around the selected electrodes. Some of the neural fibers within the EM field volume 95 will be recruited and fire, particularly those proximate to the cathodic electrode E4. Hopefully the sum of the neural fibers firing within volume 95 will mask signals indicative of pain in an SCS application, thus providing the desired therapy.

Figure 7A:
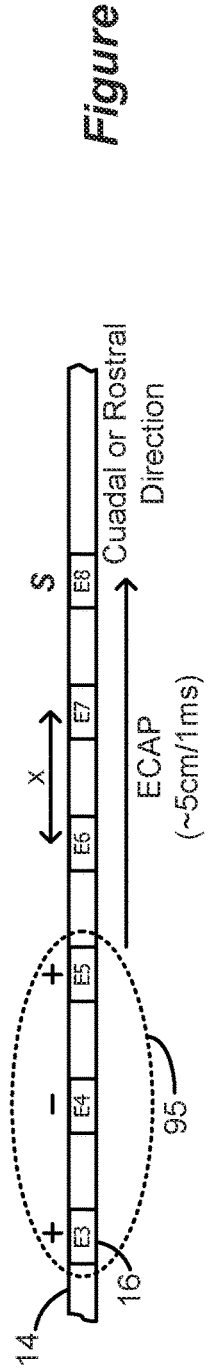
FIGS. 7A and 7B show a stimulation waveform and an evoked compound action potential.
Figure 7B:
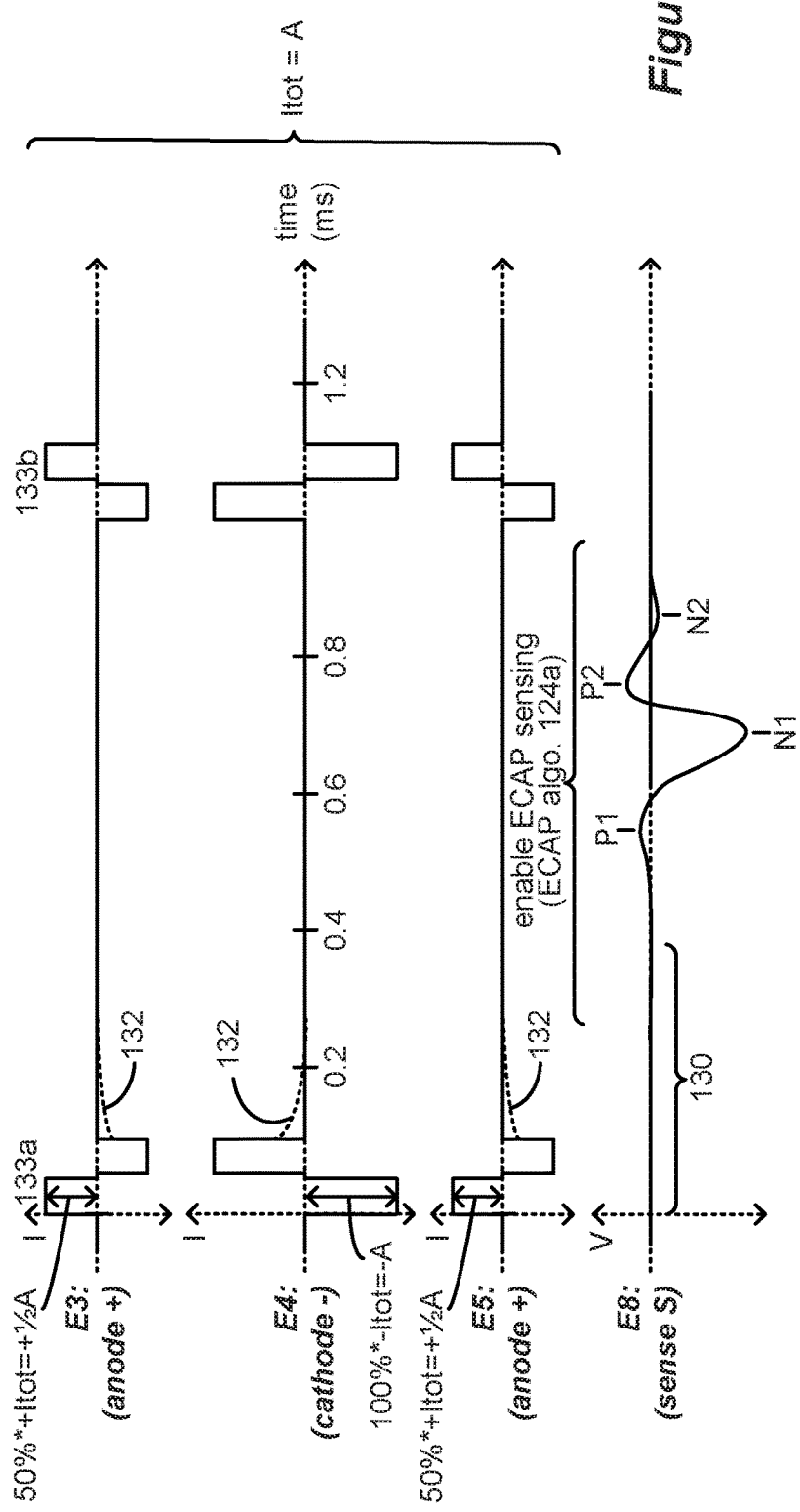

The stimulation program is defined as before by various stimulation parameters to form stimulation pulses, such as which electrodes are active for stimulation, the polarity of those electrodes, the amplitude at selected electrodes, pulse width, pulse frequency, and stimulation waveform shape (square pulses in the example shown), although these parameters are not all labeled in FIG. 7B. In the example stimulation program shown, and considering only the first phase of the biphasic pulses, electrode E4 is selected to operate as a cathode (−), and electrodes E3 and E5 are selected to operate as anodes (+). Such stimulation is usually referred to as tripolar stimulation. Tripolar stimulation is one preferred mode of providing stimulation, particularly in an SCS application, because neural fibers in the dorsal column are activated proximate to the cathode. Tripolar stimulation generally allows effective stimulation to occur at lower current amplitudes.

In the example shown, the pulses are defined with respect to a total anodic and cathodic current (collectively, Itot) that the electrodes will provide at any given time. This is desirable so that the patient's tissue will not receive a net amount of charge. The sole cathode electrode E4 provides all the total cathodic current (−Itot), and so provides 100% (−Itot), or −A. The two anode electrodes E3 and E5 must together issue the total anodic current (+Itot), and in this example, each provides 50% (+Itot), or +A/2. The anode electrodes can issue any anodic currents that together will equal +Itot (e.g., 70% +Itot and 30% +Itot). It is assumed that this stimulation program has been chosen as one that generally provides good therapeutic results for a particular patient.

Neural fibers recruited and that fire within volume 95 create a cumulative response called an Evoked Compound Action Potential, or ECAP. Once stimulation begins (at time=0), an ECAP will be produced comprising the sum of the action potentials of neural fibers recruited and hence firing in volume 95. As shown in FIG. 7B, the ECAP will move through the patient's neural tissue via neural conduction with speeds of about 3.5-7.5 cm/ms in the typical case of Aβ fibers, or 0.3-3.5 cm/ms in the case of Aδ fibers. In the example shown, the ECAP moves to the right, which may be the orthodromic direction toward the brain (rostrally) or may be the antidromic direction toward the bottom of the spinal cord of the patient (caudally). Generally, the ECAP moves both rostrally and caudally from the point of stimulation. The amplitude of the ECAP will depends on how many neural fibers are firing. Generally speaking, a primary ECAP response, e.g., the height of peak P1, can vary, usually between tens of microVolts to tens of milliVolts.

It should be noted here that compound action potentials may be evoked in various neural elements, including the neural fibers of the dorsal column, the dorsal root fibers, the dorsal root ganglia, etc. As used herein, the ECAP refers to action potentials evoked in any of the neural elements. As explained further below, an ECAP is a neural response that can be sensed at an electrode.

Referring again to FIGS. 7A and 7B, a single sense electrode (S) has been chosen to sense the ECAP as it moves past, which in this example is electrode E8. Selection of an appropriate sense electrode can be determined by an ECAP algorithm operable in the control circuitry of the IPG. Moreover, it should be noted that multiple electrodes may serve as sense electrodes. It should also be noted that in the embodiments described herein, any of the electrodes may be usable for sensing and usable for stimulation and may be selectable for either of those functions. Thus, when the disclosure refers to an electrode as a sensing electrode, it simply means that that electrode has been selected for sensing.

In FIGS. 7A and 7B, for example, assume that the pulse width (of both phases of the biphasic pulses) is 0.1 ms as shown, and that sense electrode E8 is generally 2.0 cm away from the active electrodes (and hence their EM field). When the ECAP starts to form at time=0, it will arrive at electrode E8 after some delay 130 in accordance with the speed at which the ECAP moves (e.g., 5 cm/lms). In this example, the ECAP will start to pass sense electrode E8 at 0.4 ms. Thus, the ECAP algorithm can thus enable sensing of the ECAP starting at or before time=0.4 ms after the start of the stimulation pulse. Sensing can last for as long as necessary to detect at least some aspects of the shape and size of the resulting ECAP. For example, sensing can last for a long enough time to allow the polarization and refraction peaks in the ECAP to be detected, which may comprise up to 3 ms for example. If the total duration of the ECAP is longer than the quiet period between two subsequent pulses, e.g., between pulses 133a and 133b, subsequent pulses 133b may not be enabled until the ECAP measurement has finished.

Figure 8:
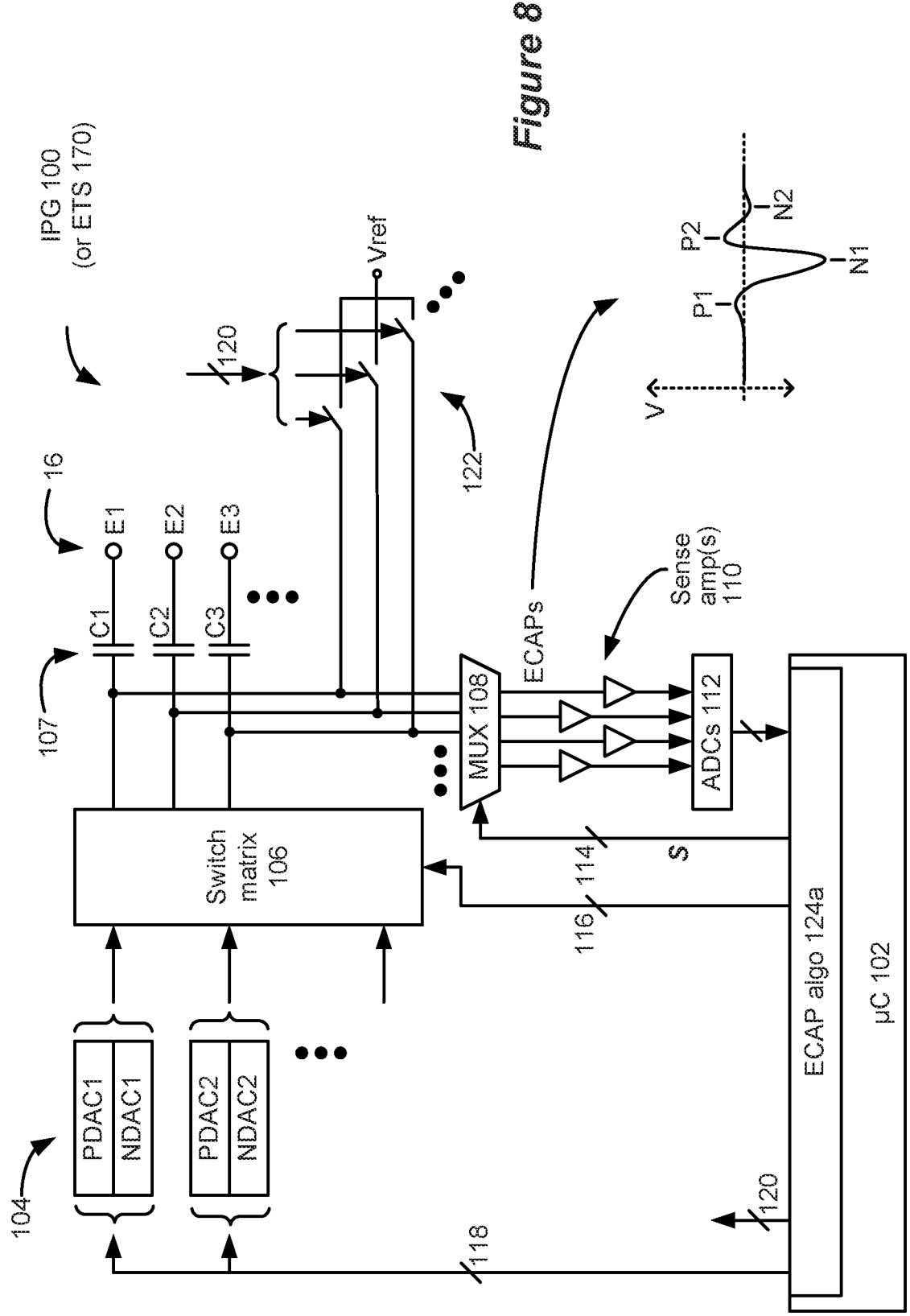
FIG. 8 shows aspects of circuitry for sensing ECAPs, reducing a stimulation artifact, and modifying stimulation based on an algorithm using ECAP parameters.

FIG. 8 shows circuitry for an improved IPG 100 operable with the disclosed technique for sensing and processing ECAP signals. Although described in the context of an IPG 100, it should be realized that the disclosed technique could also be operable in an improved external stimulator, such as an External Trial Stimulation 170 that generally mimics the operation of an IPG as explained earlier.

The IPG 100 (or ETS 170) includes control circuitry 102 into which an ECAP algorithm 124a can be programmed. Control circuitry 102 may comprise a microcontroller for example such as Part Number MSP430, manufactured by Texas Instruments, which is described in data sheets at http://www.ti.com/lsds/ti/microcontroller/16-bit_msp430/overview.page? DCMP=MCU_other& HQS=msp430, which is incorporated herein by reference, or an ARM Cortex M0+, manufactured by ARM, which is described in data sheets at http://developer.arm.com/products/processors/cortex-m/cortex-m0-plus. Other types of control circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs), for example, as described in U.S. Patent Application Publication 2012/0095529 and U.S. Pat. Nos. 9,061,140 and 8,768,453, which are incorporated herein by reference.

In the IPG 100 (or ETS 170) a bus 118 provides digital control signals to one or more Digital-to-Analog converters (DACs) 104, which are used to produce currents or voltages of prescribed amplitudes (A) for the stimulation pulses, and with the correct timing (PW, f). As shown, the DACs include both PDACs which source current to one or more selected anode electrodes, and NDACs which sink current from one or more selected cathode electrodes. In this example, a switch matrix 106 under control of bus 116 is used to route the output of one or more PDACs and one or more NDACs to any of the electrodes, which effectively selects the anode and cathode electrodes. Buses 118 and 116 thus generally set the stimulation program the IPG 100 is running. The illustrated circuitry for producing stimulation pulses and delivering them to the electrodes is merely one example. Other approaches may be found for example in U.S. Pat. Nos. 8,606,362 and 8,620,436, and U.S. Provisional Patent Application Ser. No. 62/393,003, filed Sep. 10, 2016. Note that a switch matrix 106 isn't required, and instead a PDAC and NDAC can be dedicated to (e.g., wired to) each electrode.

One or more of the electrodes 16 can be used to sense the ECAP and thus each electrode is further coupleable to at least one sense amp 110. In the example shown, there are four sense amps 110 each corresponding to a particular timing channel in which stimulation can be issued. Under control by bus 114, a multiplexer 108 can couple any of the electrodes to any of the sense amps 110 at a given time. This is however not strictly necessary, and instead each electrode can be coupleable to its own dedicated sense amp 110, or all electrodes can be selected for sensing at different times and presented by MUX 108 to a single sense amp 110. The analog waveform comprising the ECAP, described further below, is preferably converted to digital signals by one or more Analog-to-Digital converters (ADC(s)) 112, which may sample the waveform at 50 kHz for example. The ADC(s) may also reside within the control circuitry 102, particularly if the control circuitry 102 has A/D inputs.

Notice that connection of the electrodes 16 to the sense amp(s) 110 preferably occurs through the DC-blocking capacitors 107, such that capacitors are between the electrodes and the sense amp(s) 110. This is preferred so as to not undermine the safety provided by the DC-blocking capacitors 107. Once the digitized ECAP is received at the control circuitry 102, it is processed by the ECAP algorithm 124a to determine one or more ECAP features that describe the basic shape and size of the ECAP(s).

The response to stimulation can include potentials observed at different delays corresponding to different type of neural elements recruited. The delay from the stimulus can depend on the distance between the sensed electrode and the activation region where the electrical stimulus recruited most neural elements. Neural elements include axon fibers, neuron cell bodies, neuron dendrites, axon terminals, locations where fiber collaterals branch, interneurons, glial cells, or any nervous system functional part. In the specific case of the spinal cord, the sense electrodes can be placed over the dorsal column, more laterally in the epidural space towards and over the edge of dorsal horn and/or Lissauer's tract, over the dorsal root entry zone (DREZ), the rootlets, the dorsal root ganglia (DRG), the cauda equina region, the spinal nerves close to the spinal cord, the Spino-thalamic tract, and any other of the tracts surrounding the gray matter of the spinal cord.

An ECAP can contain a number of peaks or waves indicative of the different phases of the averaged or compound action potential sensed and depending on the delay with respect to the stimulus, the peak potentials can be indicative of different type of fibers activated. Axon fibers with different functions (C fibers, Aβ fibers, Aδ fibers, and others) have different diameters that correlate with different propagation velocities for the compound potentials. Conduction velocities for different axonal fiber types are known, and the conduction velocities of the ECAPs sensed in the spinal cord can be calculated to determine the originating fiber. As shown, peaks in the ECAP are conventionally labeled with P for positive peaks and N for negative peaks, with P1 comprising a first positive peak, N1 a first negative peak, P2 a second positive peak and so on. Note that not all ECAPs will have the exact shape and number of peaks as illustrated in FIG. 8, because an ECAP's shape is a function of the number and types of neural fibers that are recruited in a given volume 95.

As the ECAP propagation velocity and line shape is influenced by the number and type of neural elements recruited during the stimulus that gives rise to the ECAP, the ECAP can be used as a diagnostic tool for determining neural recruitment. Generally, one or more parameters related to the ECAP velocity and/or line shape can be correlated to a neural recruitment that results in a therapeutic effect, for example, pain relief or suppression of a side effect. The ECAP algorithm 124a (and/or 124b, FIG. 15) can be configured to determine one or more parameters of sensed ECAPs that are dependent on the stimulation and that are correlated with a therapeutic effect. Once derived or calculated, the parameter(s) can be correlated to the therapeutic effectiveness of various stimulation waveforms. Features of an ECAP that can generate such parameters include (but are not limited to):

a height of any peak (e.g., H_N1) present in the ECAP;
a peak-to-peak height between any two peaks (such as H_PtoP from N1 to P2);
a ratio of peak heights (e.g., H_N1/H_P2);
a peak width of any peak (e.g., the full width half maximum of a N1, FWHM_N1);
an area under any peak (e.g., A N1);
a total area (A_tot) comprising the area under positive peaks with the area under negative peaks subtracted or added;
a length of any portion of the curve of the ECAP (e.g., the length of the curve from P1 to N2, L_P1toN2)
any time defining the duration of at least a portion of the ECAP (e.g., the time from P1 to N2, t_P1toN2);
a time delay from stimulation to issuance of the ECAP, which is indicative of the neural conduction speed of the ECAP, and which can be useful in discerning the types of neural fibers recruited;
any mathematical combination or function of these variables (e.g., H_N1/FWHM_N1 would generally specify a quality factor of peak N1);
metrics derived using mathematical/signal processing analysis of ECAP waveforms, such as short time Fourier or wavelet transforms, principal component analysis and/or eigenvalues from principal component analysis used as coefficients for k-means clustering, etc.

The ECAP algorithm 124a (and/or 124b, FIG. 15) can be further configured to use feedback to maintain or alter stimulation to achieve the therapeutic effect. For example, the ECAP algorithm may be configured to alter, adjust, or maintain stimulation to keep one or more ECAP parameters at a certain value or within a certain range that is shown or calculated to be therapeutically effective. Thus, the ECAP algorithm can provide open loop or closed loop feedback affecting stimulus.

Electrical stimulus applied to the patient's tissue induces an EM field in the region near the stimulus electrodes. The EM field can give rise to a "stimulus artifact," which can mask the presence of an ECAP, particularly when attempting to detect an ECAP signal near the stimulus electrode(s). The stimulus artifact waveform may be several orders of magnitude greater than the ECAP and typically decays with a time constant of several hundreds of microseconds, which is sufficiently long to overlap with the ECAP response.

The masking of an ECAP by a stimulation artifact can limit the ability to use sensed ECAPs as feedback for controlling stimulation. Accurate extraction of ECAP features and determination of ECAP feedback parameters may require the detection of the N1, P1, and P2 peaks of the ECAP (see FIG. 7B). Those features may be obscured by the presence of the stimulus artifact.

Various forms of artifact reduction techniques have been described in the literature. Two common techniques are the forward masking method and the alternating polarity method. Both techniques are well described in the art. See, e.g., Akhoun, et al., *Electrically evoked compound action potential artifact rejection by independent component analysis: Technique validation*, Hear. Res. 302:60-73, (2013).

Briefly, the forward masking method involves issuing a masking pulse, which sets the neural elements in a refractory state. Then a probe pulse is issued, which allows measuring the resulting artifact (the probe artifact), absent any neural response. During subsequent measurements, the neural signal can be determined by subtracting the determined probe artifact from the overall signal, ideally leaving only the neural response (i.e., the ECAP).

The alternating polarity requires two buffers to be recorded and summed together: one buffer resulting from a cathodic-first pulse and the other resulting from an anodic-first pulse. It is assumed that the artifacts resulting from the two pulses cancel and that the neural responses add together, yielding an ECAP with double the amplitude in the summed signal.

Both the forward masking method and the alternating polarity method rely upon assumptions that are known to be only approximately true. For example, the forward masking method assumes that all the neural elements are in a refractory state when the probe stimulus is issued. However, neural elements that are not in a refractory state when the probe stimulus is issued results in the probe "artifact" signal including some contribution from neural responses, which neural responses are subsequently subtracted from resulting ECAP measurement, yielding an inaccurate ECAP measurement. Likewise, in the alternating polarity method, the cathodic-first pulse and the anodic-first pulse may not generate the same neural activity; the ECAPs may have different latencies and amplitudes, resulting in distorted ECAPs when the two ECAPs are summed together. Likewise, the assumption that the stimulation artifacts for the two polarities are equal and opposite may not hold in all cases.

Figure 15:
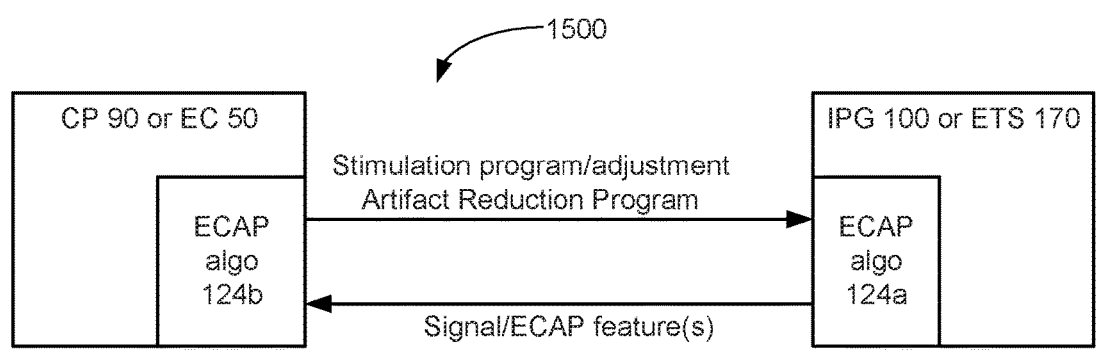
FIG. 15 shows a system for sensing a neural response, reducing a stimulation artifact, and controlling stimulation using a sensed neural response.

The inventors have developed methods of extracting ECAP features when those features are obscured by a stimulus artifact, for example, when attempting to measure an ECAP at an electrode near the location at which stimulus is applied. As mentioned above, the methods of reducing the stimulus artifact (i.e., extracting an ECAP obscured by the artifact) are embodied in the ECAP algorithm 124*a* (FIG. 8) and/or ECAP algorithm 124*b* (FIG. 15).

Figure 9:
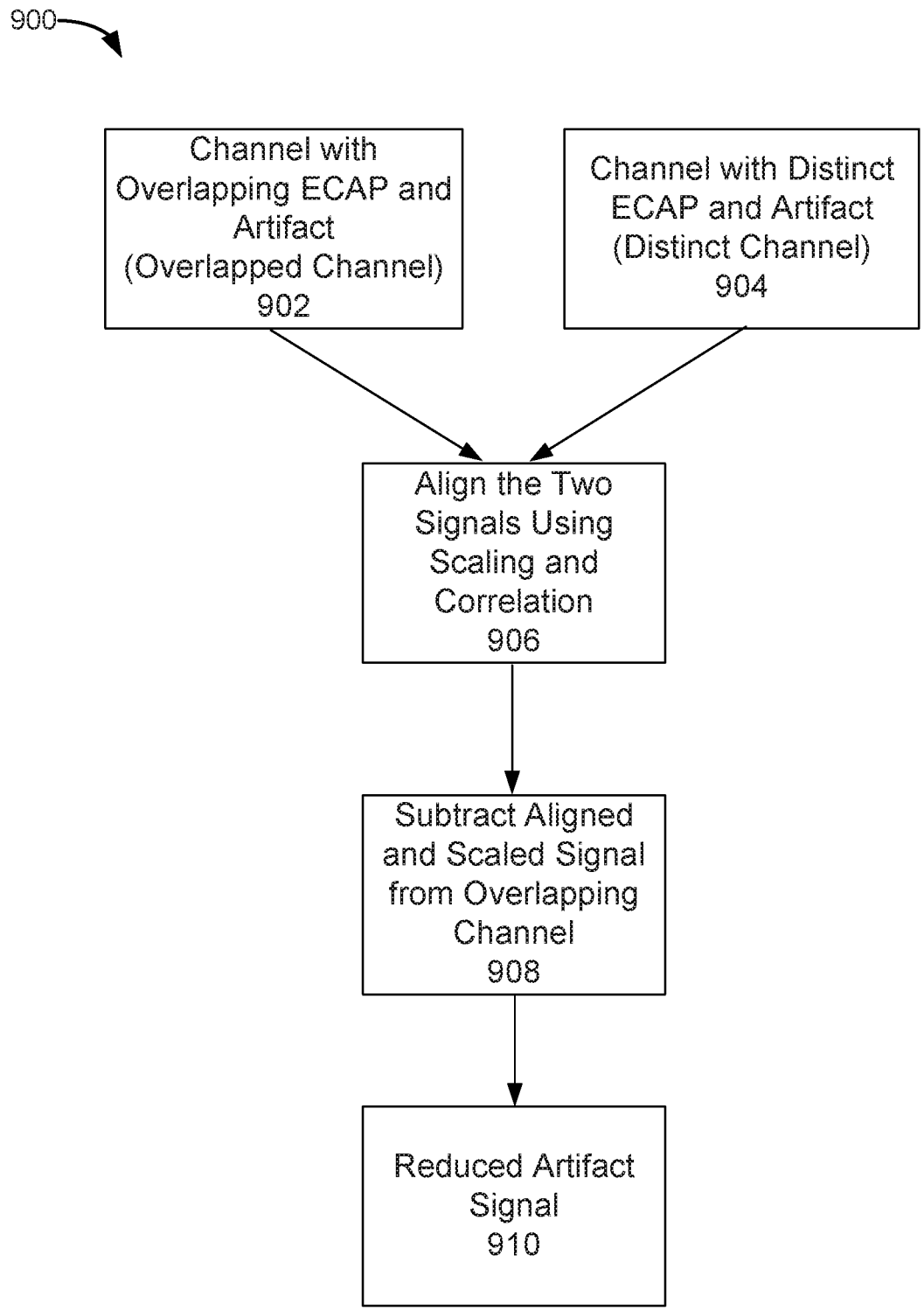
FIG. 9 shows a method for reducing a stimulation artifact.

FIGS. 9-12 illustrate an embodiment 900 of a method of reducing a stimulation artifact in an ECAP measurement. Referring to FIG. 9, measurements from two electrode channels are acquired and the measured signals are stored in buffers. On the first channel 902 a stimulation artifact overlaps and obscures an ECAP. For example, the first channel may comprise one or more electrodes located near the stimulating electrode(s). The channel with overlapping artifact and ECAP is referred to herein as the "overlapped channel." On the second channel 904, the artifact and the ECAP are distinct. The second channel may comprise one or more electrodes located distant from the stimulation electrode(s). The channel with distinct artifact and ECAP is referred to herein as the "distinct channel."

Figure 10:
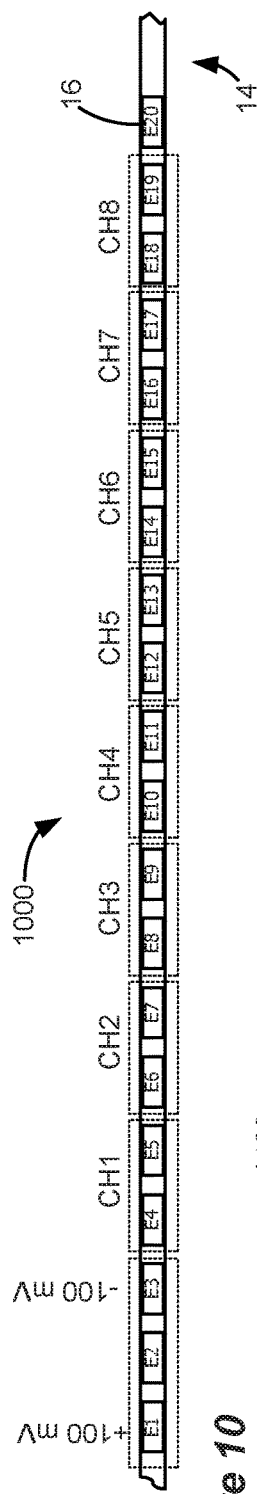
FIG. 10 shows an electrode configuration for sensing an evoked neural response and reducing a stimulation artifact.

FIG. 10 illustrates an example of an electrode/channel configuration 1000 configured to implement the embodiment 900 of the artifact reducing method. The electrode/channel configuration 1000 includes a lead 14 having a plurality of electrodes 16 (electrodes E1-E20 are illustrated in FIG. 10). A single percutaneous lead 16 is illustrated in FIG. 10, but it should be appreciated that the electrodes may be configured using multiple leads, for example multiple percutaneous leads, paddle leads, directional leads, and the like. Generally, any of the electrodes may be usable for stimulating and/or for sensing.

In the illustrated electrode/channel configuration 1000, stimulus is applied using E1 as an anode and E3 as a cathode. However, any stimulus program may be used, as known in the art. In the illustrated configuration, pairs of electrodes are defined as channels. For example, channel 1 comprises electrodes E4 and E5, channel 2 comprises electrodes E6 and E7, etc.

Figure 11A:
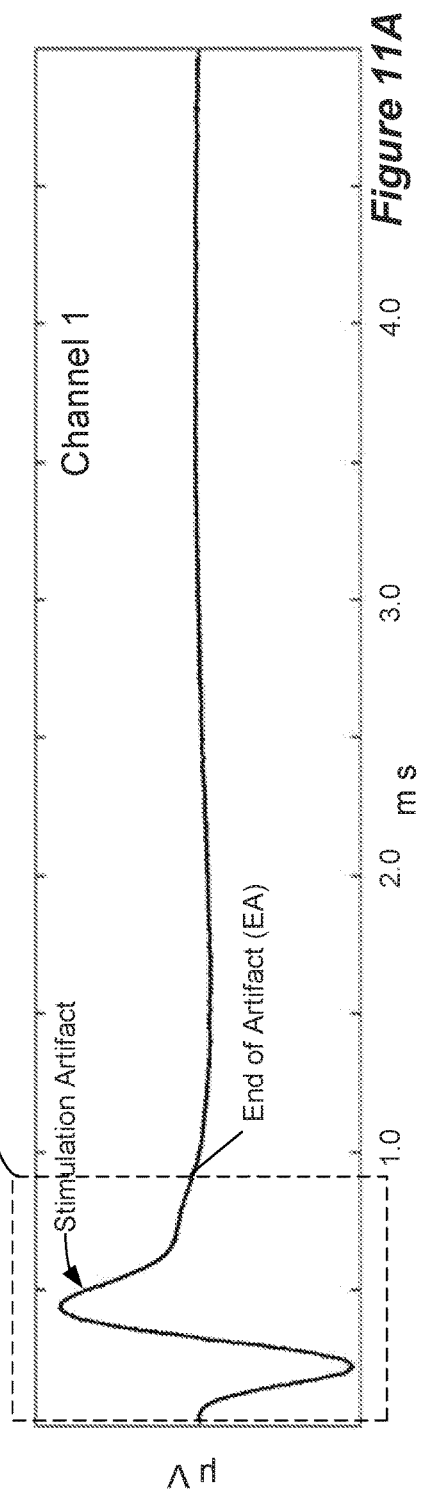
FIGS. 11A and 11B show artifact reduction in a sensed neural response.
Figure 11B:
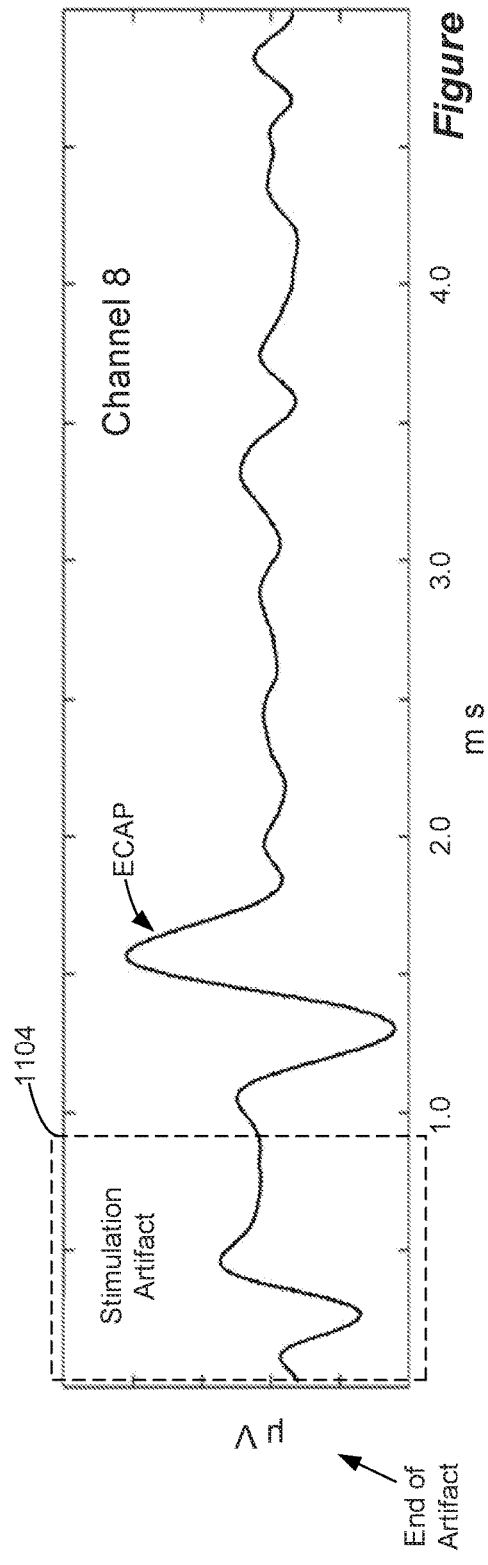

FIG. 11A illustrates a signal recorded on channel 1, the channel closest to the stimulation electrodes. The signal is dominated by the stimulation artifact, which significantly obscures the ECAP. Thus, channel 1 is an example of an "overlapped channel" in this example. FIG. 11B illustrates a signal recorded on channel 8 (electrodes E18 and E19). On channel 8 the stimulation artifact and the ECAP are clearly distinguished from each other. Thus, channel 8 is an example of a "distinct channel" in this example.

Referring again to FIG. 9, the method 900 further comprises aligning and scaling the artifact of the "distinct channel" signal 904 with the overlapped ECAP and artifact of the "overlapped channel" signal 906. First, the artifact signal is identified in the distinct channel and the beginning and end of the artifact (EA) is identified in the "distinct channel" signal. Referring to FIG. 11B, the EA is taken to be about 0.8 ms. A window is selected that includes the beginning and end of the artifact signal in the distinct channel. The window is preferably made as broad as possible, but without including the beginning of the ECAP signal. The window is illustrated as the dashed box 1104, and serves as the basis for aligning and scaling.

The window identified for the distinct channel is then aligned and scaled with respect to the overlapped channel. Because the "overlapped channel" is closer to the stimulation site than the "distinct channel," there is lag associated with the stimulation artifact sensed at the "distinct channel." Cross-correlation corrects for that lag. Generally, any type of cross-correlation function can be used to determine how much to shift the stimulation artifact of the "distinct channel" so that it most perfectly aligns with the overlapped artifact/ECAP of the "overlapped channel." With the configuration illustrated in FIG. 10, the shift may typically be about 25 μs. The dashed box 1104 of FIG. 11B shows the portion of the "distinct channel" signal that is cross-correlated and aligned with portion 1102 of the signal of the "overlapped channel." According to some embodiments, inverse stimulation polarity can be used to confirm the identity of artifact signal of the distinct channel and/or the overlapped channel. In other words, two or more stimulus pulses can be applied using opposite polarities and the stimulation artifact can be confirmed based on its polarity.

Once aligned using cross-correlation or any another temporal matching technique, the corresponding stimulation artifact of the "distinct channel" can be scaled to match closely the singular points of the artifact signal of the "overlapped channel." According to one embodiment, the scaled signal is calculated as:

$$\text{Scaled Signal} = [(\max(A) - \min(A))/(\max(B) - \min(B)) \times (B - \min(B))] + \min(A)$$

where A is the signal for the "overlapping channel" and B is the signal for the "distinct channel."

It should also be noted that the aligning and scaling of the artifact of the "distinct channel" with respect to the "overlapped channel" may be performed in parts. For example, the negative peak of the artifact may be aligned and scaled as one part and the positive peak of the artifact aligned and scaled as a separate part. Aligning and scaling the artifact signal in parts may provide a better fit. For example, if there is a high degree of overlap of the stimulation artifact and the ECAP in the "overlapped channel" it can be beneficial to align and scale the artifact signal of the "distinct channel" in parts. According to one embodiment, decision of whether to align and scale the artifact signal as a single unit or in parts is determined based on where the N1 peak of the obscured ECAP is predicted to occur vis-à-vis the obscuring stimulation artifact of the "overlapped channel." If the N1 peak of the ECAP is predicted to occur at less than the midpoint of obscuring stimulation artifact signal, then the artifact of the "distinct channel" can be scaled in parts. If the N1 peak of the ECAP is predicted to occur at the midpoint of the obscuring stimulation artifact or later, then the artifact of the "distinct channel" can be scaled as a single unit. The location of the N1 peak in the "overlapped channel" can be predicted based on the conduction velocity of the ECAP, as determined from the "distinct channel." According to some embodiments, the methods described for artifact reduction can one or more preprocessing steps. For example, each channel the signal may be broken into separate time frames where each time frame has the duration of the stimulation period, and the time frames can be averaged for each channel before doing the alignment, scaling, and subtraction of the second channel from the first. Examples of such preprocessing are described in U.S. Provisional Patent Application No. 62/614,736, filed Jan. 8, 2018, the entire contents of which are incorporated herein by reference.

Figure 12:
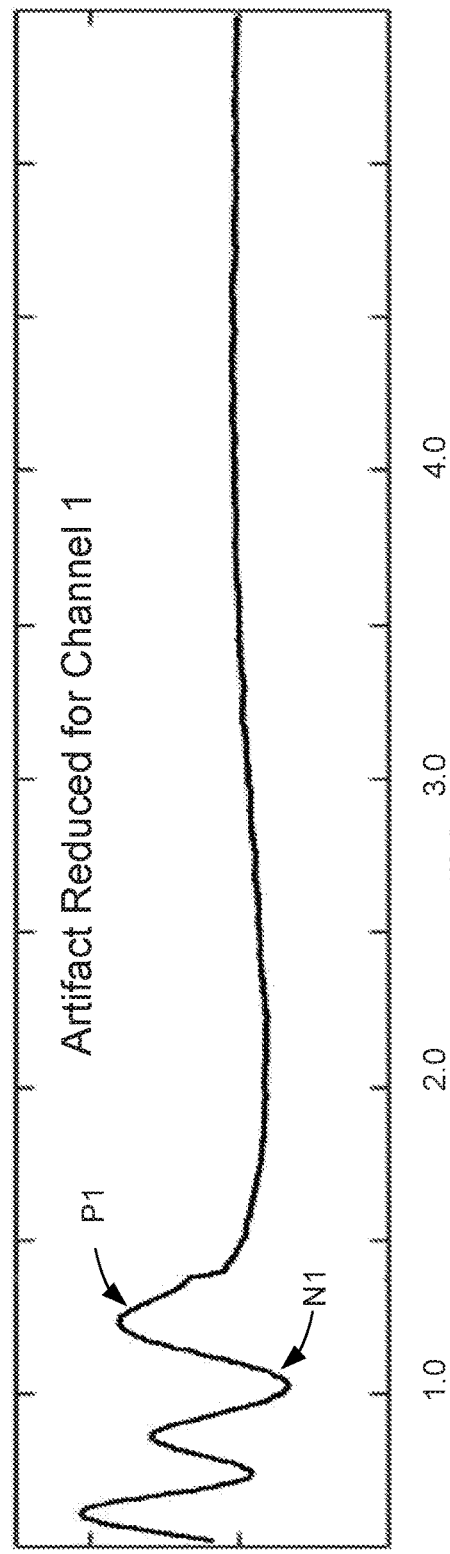
FIG. 12 shows a sensed neural response with a reduced artifact.

Referring again to FIG. 9, the aligned and scaled artifact is subtracted from the signal of the "overlapped channel" 908. The subtraction yields an ECAP for the "overlapped channel" with reduced a reduced artifact signal 910. FIG. 12 shows the result of the subtraction. It is apparent that the stimulation artifact signal is reduced compared to the stimulation artifact signal present in the channel 1 signal of FIG. 11A. The N1 and P1 peaks of the ECAP are easily discernable. The ECAP algorithm 124a (and/or 124b, FIG. 15) may be configured to determine one or more parameters of the "reduced artifact" ECAP provided by method 900 and use those parameters as feedback to control stimulation parameters, as described above.

In the example described with respect to FIGS. 11A and 11B, the polarity of the stimulation wave forms used for the overlapped channel (Channel 1) and the distinct channel (Channel 8) are the same. Thus, the polarity of the stimulation artifacts detected on those channels are the same and the stimulation artifact of the distinct channel is aligned and subtracted from the stimulation artifact of the overlapped channel to yield the reduced artifact signal illustrated in FIG. 12. An alternative embodiment may comprise using a waveform with a different polarity for detecting the stimulation artifact on the distinct channel. In that case, the polarity of stimulation artifact on the distinct channel is opposite of the polarity of the stimulation artifact on the overlapped channel. To cancel the stimulation artifacts, the stimulation artifact of the distinct channel is scaled and temporally aligned with the stimulation artifact of the overlapped channel, and then the signals are added. For ease of explanation, that process is referred to herein as subtracting the aligned and scaled stimulation artifact of the distinct channel from the stimulation artifact of the overlapped channel to yield an evoked neural response signal with a reduced artifact. Even though, mathematically, the processes is additive, the result is that the stimulation artifact is subtracted from the overlapped channel.

Figure 13:
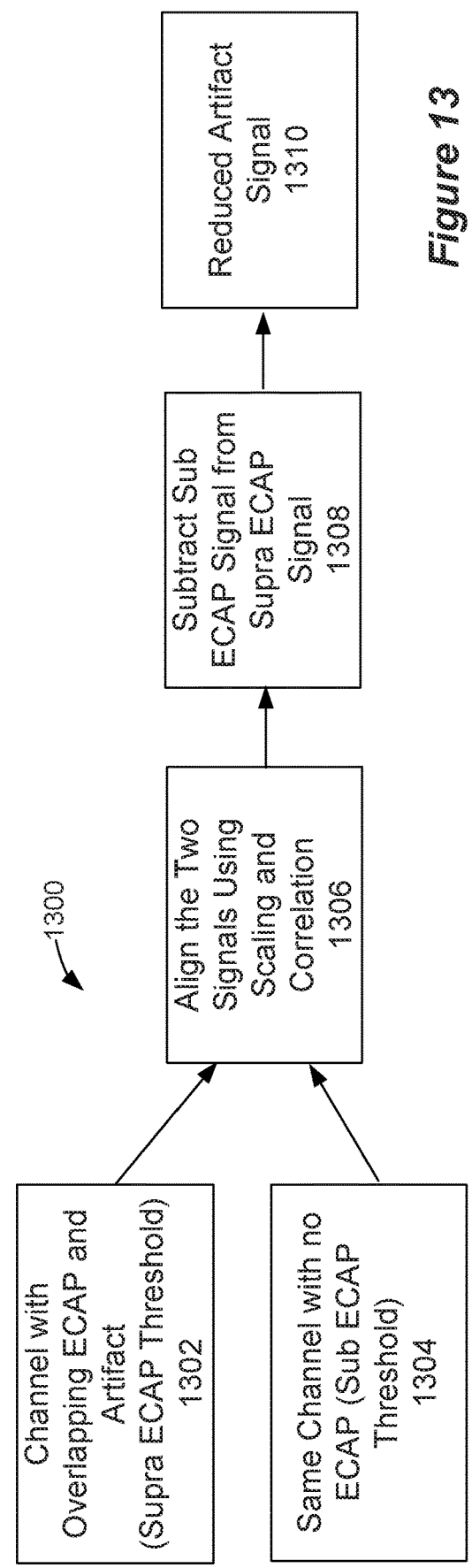
FIG. 13 shows a method of reducing a stimulation artifact.
Figure 14A:
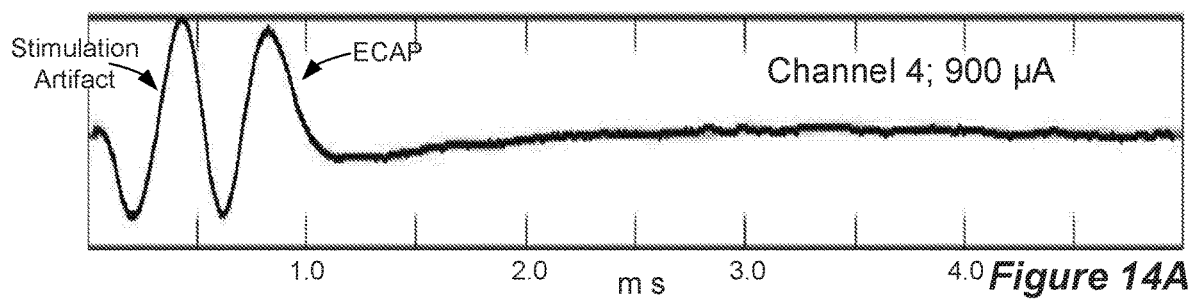
FIGS. 14A-14D show artifact reduction in a sensed neural response.
Figure 14B:
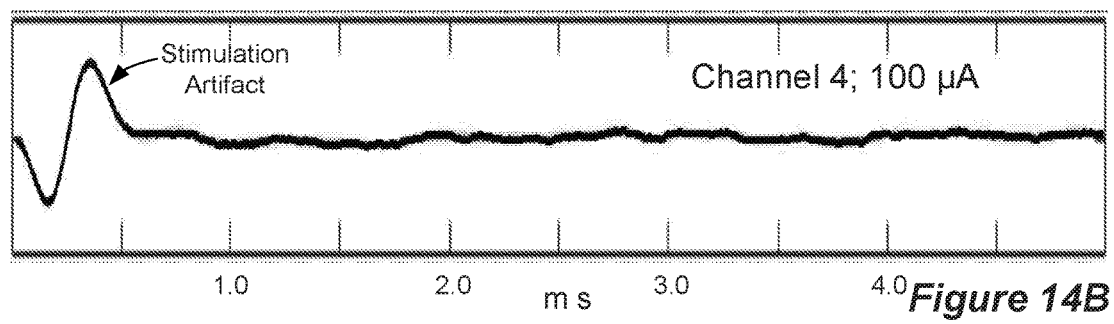
Figure 14C:
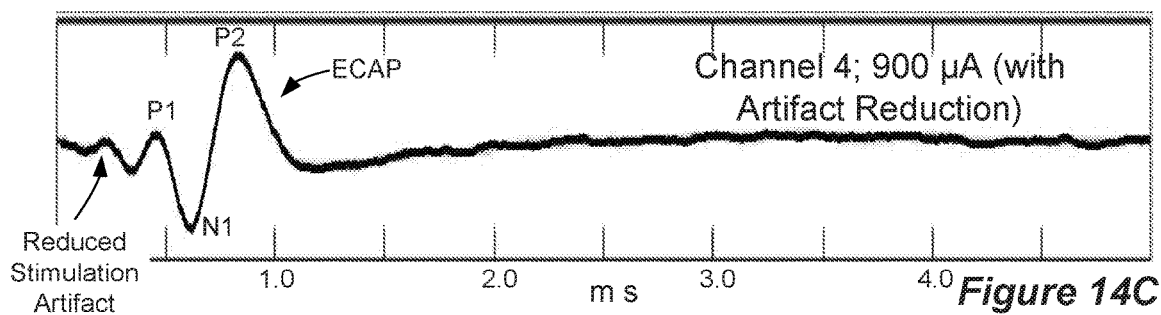
Figure 14D:
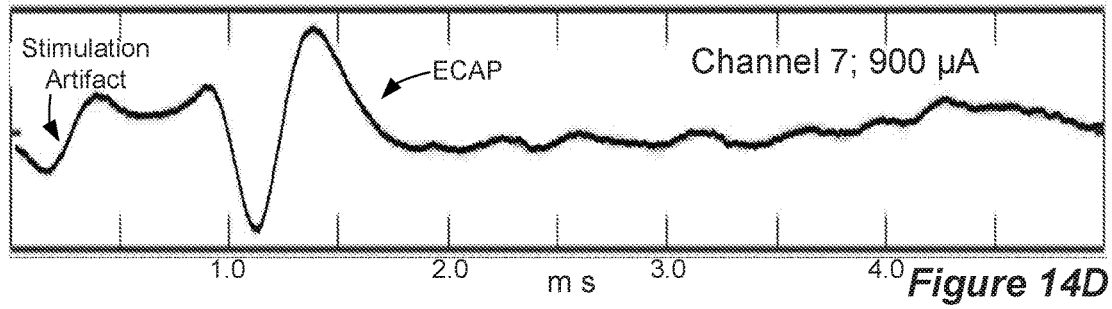

FIG. 13 illustrates another embodiment of a method 1300 of reducing a stimulation artifact in a measurement of a neural response (i.e., an ECAP). In method 1300, a stimulation waveform is applied at one or more stimulation electrodes. The intensity of the stimulation waveform is great enough to recruit sufficient neural elements to result in a measurable ECAP. Herein, the minimum intensity that results a measurable ECAP is referred to as the "ECAP threshold." Stimulation at or above the ECAP threshold is referred to supra-ECAP threshold stimulation.

Referring again to FIG. 13, supra-ECAP threshold stimulation is applied and a signal is sensed and recorded on a channel where the ECAP is obscured by a stimulation artifact 1302. For example, the signal may be recorded at a channel that is close to the site of stimulation, like the signal illustrated in FIG. 11A. As the stimulation is supra-ECAP threshold, an ECAP is present, but is obscured by the stimulation artifact, as shown in FIG. 11A.

A second stimulation waveform is then applied at the stimulation electrode(s). The second stimulation has an intensity that is insufficient to recruit enough neural elements to result in a measurable ECAP. In other words, the second stimulation is below the ECAP threshold, i.e., it is sub-ECAP threshold stimulation. Signals resulting from the sub-ECAP threshold stimulation are sensed and recorded 1304 using the same channel that was used to sense the supra-ECAP threshold signals. The recorded sub-ECAP threshold signal includes a stimulation artifact but does not include an ECAP.

Having recorded the supra-ECAP threshold signal 1302 and the sub-ECAP threshold signal 1304 measured on the same channel, the two signals are then aligned and scaled 1306, as described above with reference to the method 1300. The start and the end of the artifact can be determined using inverse polarity stimulation. The recorded sub-ECAP threshold signal is aligned with the supra-ECAP threshold signal using cross-correlation. The aligned sub-ECAP threshold signal is then scaled to match the supra-ECAP threshold signal, as described above. As described above, the aligning and scaling may be performed in segments or as a single unit.

The aligned and scaled sub-ECAP threshold signal is subtracted from the supra-ECAP threshold signal 1308. The subtraction yields an ECAP signal with a reduced artifact signal 1310. The "reduced artifact" ECAP can be used as feedback control for stimulation, as described above.

FIGS. 14 A-D illustrate an application of the method 1300. FIG. 14 A shows a signal recorded using a channel (referred to as channel 4) near electrodes applying supra-ECAP threshold stimulus (stimulation intensity of 900 µA). An ECAP is apparent but is partially obscured by a stimulation artifact. FIG. 14B shows a signal recorded on the same channel, but using a sub-ECAP threshold stimulation intensity of 100 µA. A stimulation artifact is present but no ECAP is apparent. FIG. 14C shows the result of the artifact reduction 1300. After aligning and scaling the artifact from FIG. 14B and subtracting the aligned/scaled signal from the signal of 14 A, the stimulation artifact is reduced and the ECAP is more clearly visible. For comparison, a signal recorded at a more distant channel (channel 7) with a supra-ECAP threshold stimulation intensity of 900 µA is shown in FIG. 14D. As expected, the signal shown in FIG. 14D has a distinct stimulation artifact and ECAP.

Referring again to FIG. 8, one or more aspects the methods described above for reducing the stimulation artifact in an ECAP measurement can be embodied in the ECAP algorithm 124a of the microcontroller of the IPG 100 (or ETS 170). Alternatively (or in addition), one or more aspects of the methods may be embodied in an external device, such as a clinician programmer 90 (FIG. 3) or an external controller (FIG. 2). FIG. 15 illustrates aspects of a system 1500 for sensing and recording signals on one or more channels of electrodes and configuring an IPG 100 (or ETS 170) to execute the method(s) of stimulation artifact reduction described above. One aspect of the system 1200 is an improved IPG 100 (or ETS 170), as described above, with reference to FIG. 8. As mentioned above, the IPG 100 (or ETS 170) includes control circuitry 102 into which an ECAP algorithm 124a can be programmed. As also noted above, the ECAP algorithm can alternatively operate with the assistance of external devices, as shown in FIG. 3, which shows an external programming device (such as the clinician programmer 90 or external controller 50) in wireless communication with the IPG 100 (or ETS 170). Generally, any external device may be appropriately configured device, including a personal computer or a personal computing device such as a tablet or smart phone executing one or more applications embodying aspects of the ECAP algorithm. Thus, another aspect of the system 1500 may be an external device, such as a CP 90 (or EC 50), or the like. An ECAP algorithm 124b is included in the external device, which can receive information from the IPG 100 (or ETS 170) regarding the signals it measures, process the signals, and send a stimulation program (or adjustment) to the IPG. ECAP algorithm 124a again operates in the IPG 100 (or ETS 170), but in this example, off-loads signal analysis and stimulation program adjustment to ECAP algorithm 124b in the external device. A system 1500 as shown in FIG. 15 is particularly useful when fitting the implant patient, i.e., when determining a stimulation program that would be useful in treating the patient's symptoms. One skilled in the art will understand that the ECAP algorithm 124a and 124b and/or any supporting user interface program will comprise instructions that can be stored on non-transitory machine-readable media (i.e., computer-readable medium), such as magnetic, optical, or solid-state memories. Such memories may be within the IPG or ETS itself (i.e., stored in association with control circuitry 102), within the external system, or readable by the external system (e.g., memory sticks or disks). Such memories may also include those within Internet or other network servers, such as an implantable medical device manufacturer's server or an app store server, which may be downloaded to the external system.

Figure 16:
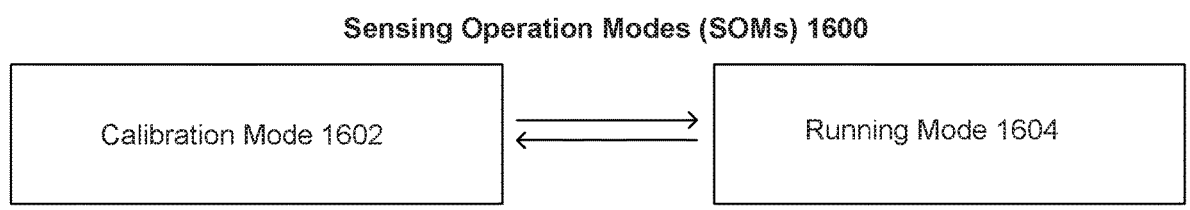
FIG. 16 shows sensing operation modes of a system for sensing a neural response, reducing a stimulation artifact, and controlling stimulation using a sensed neural response.

Referring to FIG. 16, embodiments of the neuromodulation system and algorithm may comprise two sensing operating modes (SOMs) 1600—a calibration mode 1602 and a running mode 1604. The calibration mode 1602 will typically be executed during the fitting process with the aid of the clinician programmer (CP) 90, though aspects of the calibration mode may be executed using the external controller (EC) 50. During the calibration mode 1602, the user, typically a clinician, is presented with a user interface, such as a graphical user interface (GUI). The interface is configured to present the user with a representation of the electrical signals provided to and sensed at the various available implanted electrodes (channels). The interface also allows user to modify the stimulation parameters of the IPG 100 and to visualize how changing the stimulation parameters affects the sensed signals. The user can thereby determine which channels to use as sensing channels and determine if artifact reduction is needed for signals sensed on those channels. For example, the user can select one or more channels as "overlapped channels" and as "distinct channels" as per method 900, described above. The user can determine, or have the algorithm determine the parameters for artifact reduction, such as the end of artifact and end of ECAP values used by the method. The appropriate artifact reduction parameters can be programmed into the IPG 100 (or ETS 170), so that the artifact reduction method is applied each time the IPG 100 (or ETS 170) makes a measurement on an "overlapped channel" during the running mode. An example of a system for interacting with the IPG 100 is described in "Precision Spectra™ System Programming Manual," Boston Scientific Corp., 90834018-18 Rev A (2016).

The running mode 1604 is generally executed by programmed circuitry within the IPG 100 (or ETS 170), as described with reference to FIG. 8. The running mode may execute the method(s) of artifact reduction for any measurements on channels having a stimulation artifact overlapping with an ECAP signal. The running mode may also periodically instantiate a calibration mode to recalibrate the artifact reduction parameters. During (re)calibration, the distinct artifact signal may be (re)confirmed using inverse polarity stimulation and the alignments/scaling parameters may be (re)calibrated. The calibration mode may be executed entirely within the IPG 100 (or ETS 170) or may be executed in conjunction with an external device, such as EC 50, CP 90, an application on a personal computing device, etc.

Although particular embodiments have been shown and described, the above discussion should not limit the present invention to these embodiments. Various changes and modifications may be made without departing from the spirit and scope of the present invention. Thus, the present invention is intended to cover equivalent embodiments that may fall within the scope of the present invention as defined by the claims.

What is claimed is:

1. A neuromodulation system comprising:
a first device comprising a non-transitory computer readable medium comprising instructions, which when executed by a microprocessor configure the microprocessor to:
cause one or more electrodes useable for stimulation to issue one or more stimulation waveforms to a patient's neural elements,
receive a first signal from a first one or more electrodes useable for sensing, the first signal comprising a first stimulation artifact and a first evoked neural response signal, wherein the first one or more electrodes usable for sensing are located a first distance from the one or more electrodes useable for stimulation where the first stimulation artifact overlaps the first evoked neural response,
receive a second signal from a second one or more electrodes useable for sensing, the second signal comprising a second stimulation artifact and a second evoked neural response signal, wherein the second one or more electrodes usable for sensing are located a second distance from the one or more electrodes useable for stimulation where the second stimulation artifact does not overlap the second evoked neural response signal, and
reducing the first stimulation artifact using the second signal.

2. The neuromodulation system of claim 1, wherein the first one or more electrodes usable for sensing are closer to the one or more electrodes usable for stimulating than are the second one or more electrodes usable for sensing.

3. The neuromodulation system of claim 1, wherein reducing the first stimulation artifact comprises:
aligning and scaling the second stimulation artifact with respect to the first stimulation artifact, and
subtracting the aligned and scaled second stimulation artifact from the first stimulation artifact.

4. The neuromodulation system of claim 3, wherein aligning the second stimulation artifact with respect to the first stimulation artifact comprises cross-correlation.

5. The neuromodulation system of claim 1, wherein the instructions further configure the microprocessor to determine a beginning and an end of the first stimulation artifact using inverse stimulation polarity.

6. The neuromodulation system of claim 1, wherein the first device is an implantable pulse generator (IPG) or an external trial stimulator (ETS).

7. The neuromodulation system of claim 1, wherein the first device is an external device.

8. The neuromodulation system of claim 7, further comprising an IPG or an ETS.

9. The neuromodulation system of claim 1, wherein the instructions further configure the microprocessor to determine one or more parameters of the first evoked neural response signal.

10. The neuromodulation system of claim 9, wherein the instructions further configure the microprocessor to alter the one or more stimulation waveforms based on the one or more features determined from the first evoked neural response signal.

11. A method of measuring an evoked neural response, the method comprising:
 causing one or more electrodes useable for stimulation to issue one or more stimulation waveforms to a patient's neural elements,
 receiving a first signal from a first one or more electrodes useable for sensing, the first signal comprising a first stimulation artifact and a first evoked neural response signal, wherein the first one or more electrodes usable for sensing are located a first distance from the one or more electrodes useable for stimulation where the first stimulation artifact overlaps the first evoked neural response,
 receiving a second signal from a second one or more electrodes useable for sensing, the second signal comprising a second stimulation artifact and a second evoked neural response signal, wherein the second one or more electrodes usable for sensing are located a second distance from the one or more electrodes useable for stimulation where the second stimulation artifact does not overlap the second evoked neural response signal, and
 reducing the first stimulation artifact using the second signal.

12. The method of claim 11, wherein reducing the first stimulation artifact comprises:
 aligning and scaling the second stimulation artifact with respect to the first stimulation artifact, and
 subtracting the aligned and scaled second stimulation artifact from the first stimulation artifact.

13. The method of claim 12, wherein aligning the second stimulation artifact with respect to the first stimulation artifact comprises cross-correlation.

14. The method of claim 11, further comprising determining a beginning and an end of the first stimulation artifact using inverse stimulation polarity.

15. The method of claim 11, further comprising determining one or more parameters of the first evoked neural response signal.

16. The method of claim 15, further comprising altering the one or more stimulation waveforms based on the one or more features determined from the first evoked neural response signal.

17. A non-transitory computer readable medium configured to cause a microprocessor to:
 cause one or more electrodes useable for stimulation to issue one or more stimulation waveforms to a patient's neural elements,
 receive a first signal from a first one or more electrodes useable for sensing, the first signal comprising a first stimulation artifact and a first evoked neural response signal, wherein the first one or more electrodes usable for sensing are located a first distance from the one or more electrodes useable for stimulation where the first stimulation artifact overlaps the first evoked neural response,
 receive a second signal from a second one or more electrodes useable for sensing, the second signal comprising a second stimulation artifact and a second evoked neural response signal, wherein the second one or more electrodes usable for sensing are located a second distance from the one or more electrodes useable for stimulation where the second stimulation artifact does not overlap the second evoked neural response signal, and
 reduce the first stimulation artifact using the second signal.

* * * * *